United States Patent
Lee et al.

(10) Patent No.: US 10,583,117 B2
(45) Date of Patent: Mar. 10, 2020

(54) OXO-M AND 4-PPBP INDUCTION OF TENOGENIC DIFFERENTIATION OF PERIVASCULAR TENDON STEM CELLS

(71) Applicant: The Trustees of Columbia University in the City of New York, New York, NY (US)

(72) Inventors: Chang Hun Lee, New York, NY (US); Solaiman Tarafder, West New York, NY (US); Esther Chen, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/133,076

(22) Filed: Sep. 17, 2018

(65) Prior Publication Data

US 2019/0015386 A1    Jan. 17, 2019

Related U.S. Application Data

(63) Continuation-in-part of application No. PCT/US2017/022751, filed on Mar. 16, 2017.

(60) Provisional application No. 62/309,050, filed on Mar. 16, 2016, provisional application No. 62/668,582, filed on May 8, 2018.

(51) Int. Cl.

| | |
|---|---|
| *A61K 31/4015* | (2006.01) |
| *A61P 31/00* | (2006.01) |
| *A61P 37/06* | (2006.01) |
| *A61K 9/16* | (2006.01) |
| *A61L 27/18* | (2006.01) |
| *A61L 27/54* | (2006.01) |
| *A61K 31/196* | (2006.01) |
| *A61K 9/00* | (2006.01) |
| *A61L 27/56* | (2006.01) |
| *B33Y 80/00* | (2015.01) |

(52) U.S. Cl.
CPC ........ *A61K 31/4015* (2013.01); *A61K 9/0019* (2013.01); *A61K 9/0024* (2013.01); *A61K 9/16* (2013.01); *A61K 9/1635* (2013.01); *A61K 31/196* (2013.01); *A61L 27/18* (2013.01); *A61L 27/54* (2013.01); *A61L 27/56* (2013.01); *A61P 31/00* (2018.01); *A61P 37/06* (2018.01); *B33Y 80/00* (2014.12); *A61L 2300/412* (2013.01); *A61L 2300/622* (2013.01)

(58) Field of Classification Search
CPC ................................................ A61K 31/4015
See application file for complete search history.

(56) References Cited

U.S. PATENT DOCUMENTS

2018/0085493 A1    3/2018    Lee et al.

FOREIGN PATENT DOCUMENTS

| WO | 2016149153 | 9/2016 |
| WO | 2017161140 | 9/2017 |

OTHER PUBLICATIONS

Lee, et al., Harnessing endogenous stem/progenitor cells for tendon regeneration, J. Clin Invest., 2015, pp. 2690-2701, vol. 125.
Lake, et al., Animal models of tendinopathy, Disabil. Rehabil., 2008, pp. 1530-1541, vol. 30.
Lee, et al.,Three-dimensional printed multiphase scaffolds for regeneration of periodontium complex, Tissue Eng. Parl A, 2014, pp. 1342-1351, vol. 20.
Lee, et al., CTGF directs fibroblast differentiation from human mesenchymal stem/stromal cells and defines connective tissue healing in a rodent injury model, J. Clin. Invest., 2010, pp. 3340-3349, vol. 120.
Lee, et al., Regeneration of the articular surface of the rabbit synovial joint by cell horning: a proof of concept study Lancet, 2010, pp. 440-448, vol. 376.
Lee, et al., Protein-releasing polymeric scaffolds induce fibrochondrocytic differentiation of endogenous cells for knee meniscus regeneration in sheep, Sci. Transl. Med., 2014, 6(266):266ra171.
Linseman, et al., Attenuation of focal adhesion kinase signaling following depletion of agonist-sensitive pools of phosphatidylinositol 4, 5-bisphosphate, J. Neurochem, 1999, pp. 1933-1944, vol. 73.
Lipinski, C., Drug-like properties and the causes of poor solubility and poor permeability, Pharmacol. Toxicol. Methods, 2000, pp. 235-249, vol. 44.
Liu, et al., What are the validated animal models for tendinopathy?, Scand. J. Med. Sci. Sports, 2011, pp. 3-17, 21 vol.
Tan, et al., The σ1 receptor agonist 4-PPBP elicits ERK1/2 phosphorylation in primary neurons: A possible mechanism of neuroprotective action, Neuropharmacology, 2010, pp. 416-424, vol. 59.
Tempfer, et al., Perivascular cells of the supraspinatus tendon express both tendon-and stem cell-related markers, Histochem. Cell Biol., 2009, pp. 733-741, vol. 131.
Varde and Pack, Microspheres for controlled release drug delivery, Expert opinion on biological therapy, 2004, pp. 35-51, vol. 4.

*Primary Examiner* — Yong L Chu
(74) *Attorney, Agent, or Firm* — Beusse Wolter Sanks & Maire; Timothy Van Dyke

(57) ABSTRACT

Provided herein are compositions including oxotremorine (e.g., oxotremorine methiodide or Oxo-M) and 4-PPBP (e.g., 4-PPBP maleate). Also provided are methods of treating a connective tissue defect in a subject with oxotremorine and 4-PPBP. In addition, provided are scaffolds and methods of making same that include multiple fibers that include Oxo-M, 4-PPBP, and optionally icariin or kartogenin.

21 Claims, 21 Drawing Sheets

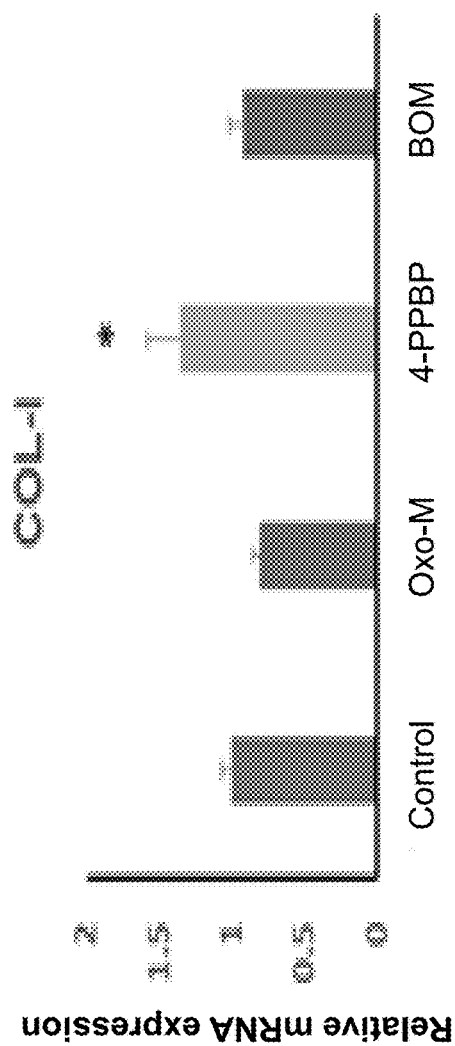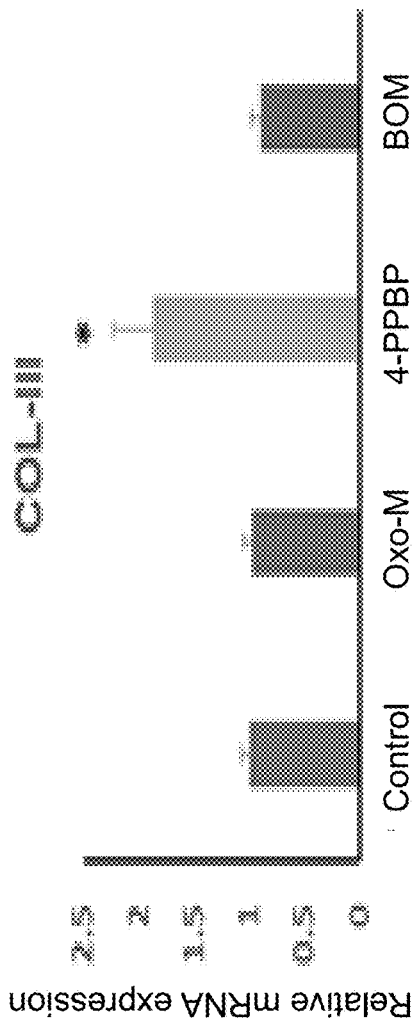

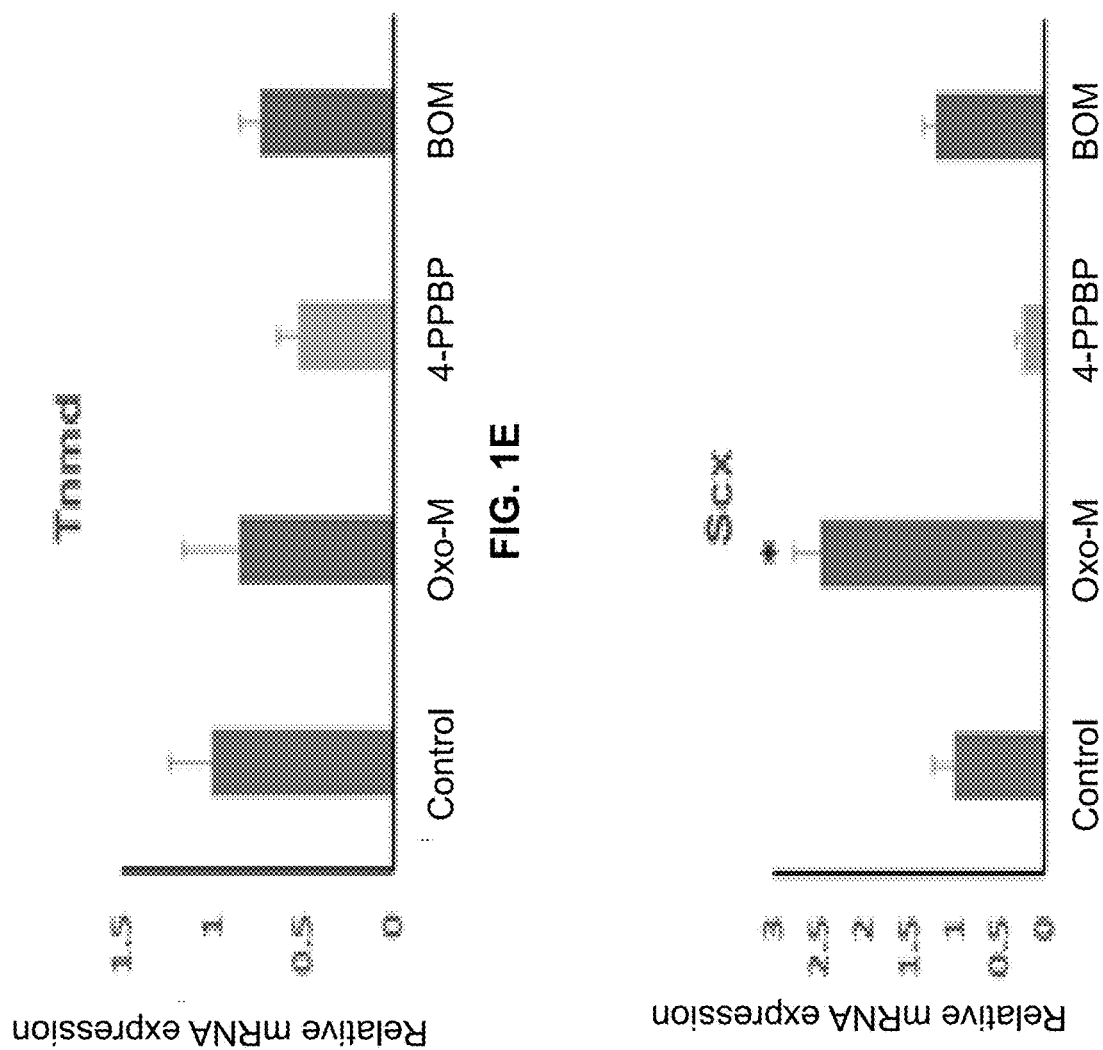

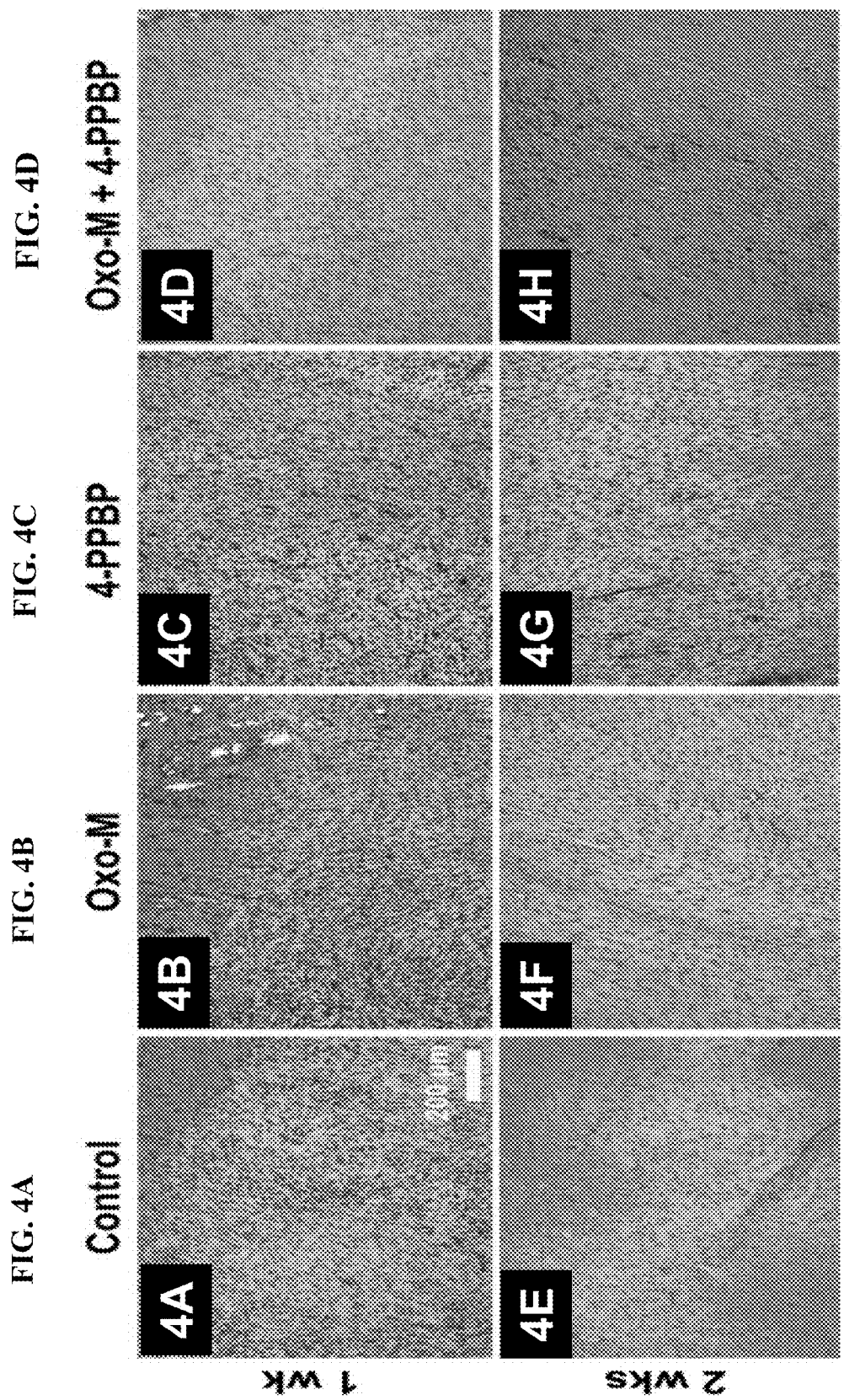

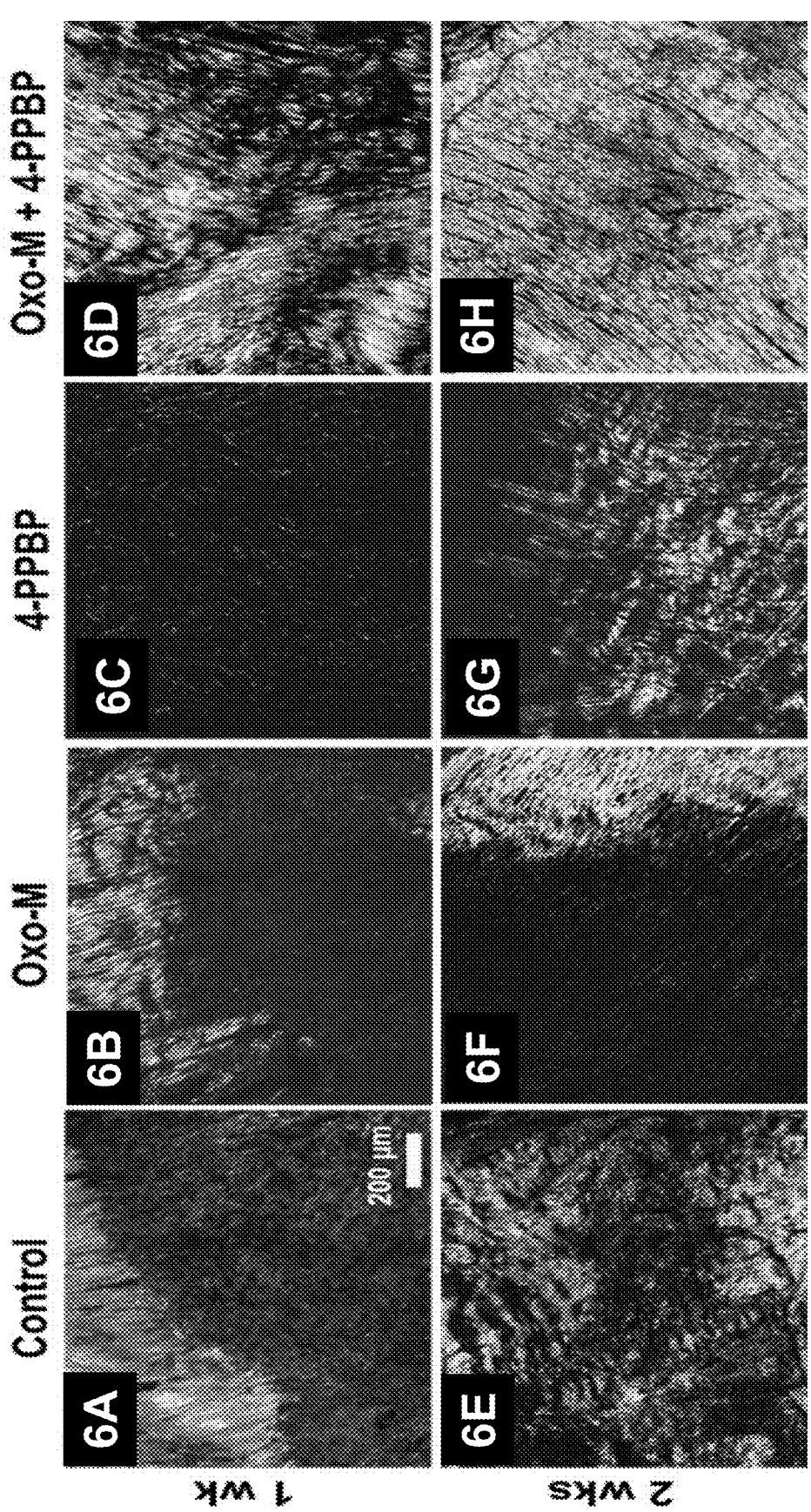

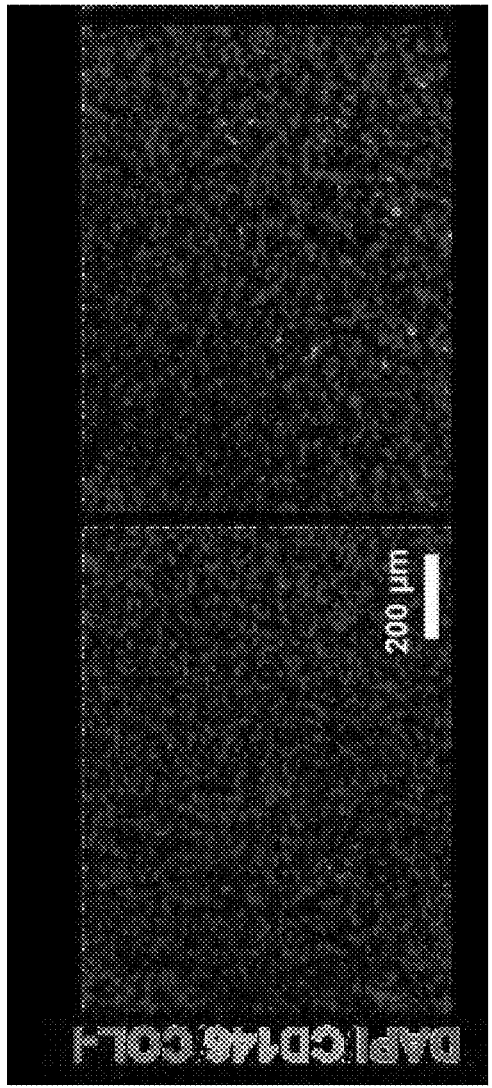
FIG. 7A
FIG. 7B
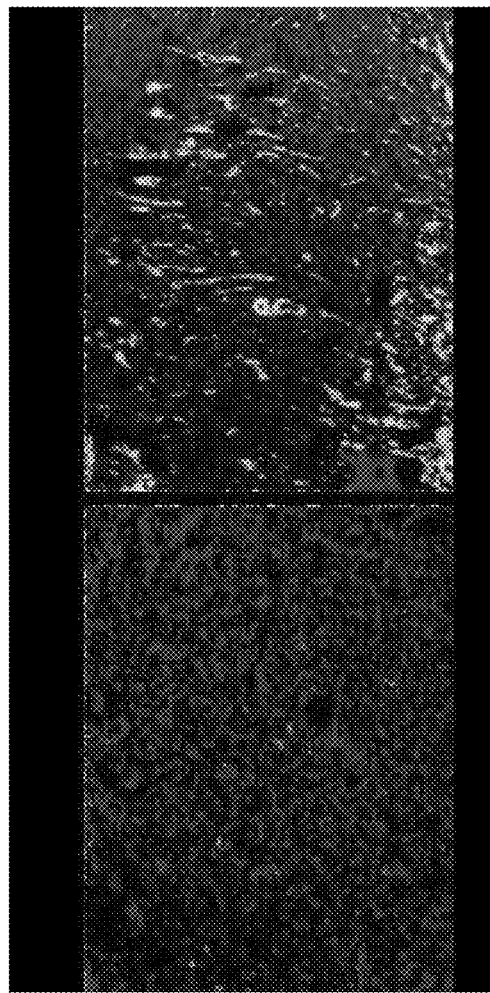
FIG. 7C
FIG. 7D

OXO-M AND 4-PPBP INDUCTION OF TENOGENIC DIFFERENTIATION OF PERIVASCULAR TENDON STEM CELLS

CROSS-REFERENCE TO RELATED APPLICATIONS

This application is a continuation-in-part from PCT/US17/22751 filed Mar. 16, 2017 which claims the benefit of U.S. Provisional Application Ser. No. 62/309,050, filed Mar. 16, 2016 and claims priority under 35 USC 119 and 120 to the foregoing applications.

The present application also claims the benefit of U.S. Provisional Application No. 62/668,582 filed May 8, 2018, which are incorporated herein by reference in its entirety.

BACKGROUND OF THE INVENTION

Current stem cell-based strategies for tissue regeneration involve ex vivo manipulation of these cells to confer features of the desired progenitor population. Despite being a valid approach, cell transplantation has encountered crucial barriers in therapeutic translation, including immune rejection; pathogen transmission; potential tumorigenesis; issues associated with packaging, storage, and shipping; and difficulties in clinical adoption and regulatory approval.

Perivascular tendon stem/progenitor cells (PTSCs) are a small population of multipotent cells that play a critical role in tendon healing and regeneration. While connective tissue growth factor (CTGF) has been shown to induce PTSCs to differentiate into tendon cells and helps to recruit PTSCs to the site of injury following tendon rupture, the clinical use of CTGF as a therapy for tendon injury may be limited by the many challenges typically associated with biologics.

CTGF is known to recruit CD146+ perivascular tendon stem/progenitor cells (PTSCs) to the site of injury following tendon rupture; induce differentiation of PTSCs into tendon cells; and regenerate fully transected tendons (Lee, et al., *J. Clin. Invest.* 125:2690-2701, 2015). CTGF-induced proliferation and tenogenic differentiation of PTSCs are regulated by the focal adhesion kinase (FAK) and extracellular signal-regulated kinase (ERK) ½ pathway (Lee, et al., 2015, supra), consequently leading to tendon regeneration in rats.

CTGF can selectively enrich PTSCs in the early phase of tendon healing and induce tenogenic differentiation in the later phase (Lee, et al., 2015, supra). Localized delivery of CTGF can promote healing and regeneration of transected tendons in vivo by inducing a transient increase in PTSCs (Lee, et al., 2015, supra).

The PTSCs are a small population of multipotent cells that play a critical role in tendon healing and regeneration, and the stimulation of tenogenic differentiation of PTSCs is a key to regenerate torn tendons (see, e.g., Lee, et al., 2015, supra). PTSCs can be found in the perivascular niche and express both tendon- and stem cell-like characteristics (Tempfer, et al., *Histochem. Cell Biol.* 131:733-741, 2009; Lee, et al., 2015, supra).

Despite these promising results, however, the clinical use of CTGF as a therapy for tendon injury may be limited by the many challenges typically associated with biologics, which include high cost, immunogenicity, and the necessity for complex delivery systems.

Oxotremorine M (Oxo-M) and PPBP maleate (4-PPBP) are receptor agonists which activate the same signaling pathway that regulates CTGF-mediated tenogenic differentiation of PTSCs. Oxo-M has been identified as a muscarinic receptor agonist that can elicit FAK signaling in neuronal cells (Linseman, et al., *J. Neurochem.* 73:1933-1944, 1999). 4-phenyl-1-(4-phenylbutyl) piperidine (4-PPBP) is a small molecule $\sigma_1$ receptor agonist that can elicit ERK1/2 phosphorylation in primary neurons (Tan, et al., *Neuropharmacology* 59:416-424, 2010).

SUMMARY OF THE INVENTION

A combination of two small molecule compounds oxotremorine (Oxo-M) and PPBP (4-PPBP maleate), have been shown to induce differentiation of PTSCs into tendon-like cells. These compounds activate the same signaling pathway that regulates CTGF-mediated differentiation of PTSCs and, when combined, can be more effective than even CTGF at increasing expression of tendon markers. This combinatorial small molecule compound approach can be adapted for tendon or ligament therapy or for soft tissue research applications.

Studies described herein show the combination of Oxo-M and 4-PPBP can induce tenogenic differentiation of PTSCs; Oxo-M significantly increases PTSC expression of tenogenic markers tenascin-C, vimentin, and scleraxis after 1 week of treatment in vitro; 4-PPBP significantly increases PTSC expression of tenogenic markers collagen I and III after 1 week of treatment in vitro; and the combined administration of Oxo-M and 4-PPBP has synergistic effects on tenogenic differentiation and increases expression of tenogenic markers collagen I and II, vimentin, tenomodulin, and scleraxis to comparable or higher levels than CTGF stimulation.

One aspect provides a composition. In some embodiments, the composition includes oxotremorine (e.g., oxotremorine methiodide, Oxo-M) and PPBP (e.g., 4-PPBP maleate). In certain embodiments, the concentration of Oxo-M is between about 10 µM and about 100 mM, or between about 100 µM and about 10 mM. In particular embodiments the concentration of Oxo-M is about 1 mM. In other embodiments the concentration of 4-PPBP is between about 100 nM and about 1 mM, or between about 1 µM and about 100 µM. In yet other embodiments the concentration of 4 PPBP is about 10 µM. In further embodiments the concentration of Oxo-M is about 1 mM and the concentration of 4 PPBP is about 10 µM. In some embodiments, the composition is a pharmaceutical composition including oxotremorine or a salt thereof (e.g., Oxo-M), 4-PPBP or a salt thereof (e.g., 4-PPBP maleate), and a pharmaceutically acceptable excipient. In some embodiments, the composition or pharmaceutical composition further includes a matrix material, a surgical adhesive, or a fibrin glue. In additional embodiments the composition or pharmaceutical composition further includes an antibiotic, an anti-inflammatory, a cytokine, a growth factor, or a stem cell. In still other embodiments the Oxo M and said 4-PPBP are encapsulated in a microsphere.

Another aspect provides a method of treating a connective tissue defect in a subject. In some embodiments, the method includes administering oxotremorine or a salt thereof (e.g., Oxo-M) and 4-PPBP or a salt thereof (e.g., 4-PPBP maleate) to a subject in need thereof. In some embodiments, the method includes providing a pharmaceutical composition comprising an effective amount, or a therapeutically effective amount, of oxotremorine or a salt thereof (e.g., Oxo-M), an effective amount, or a therapeutically effective amount, of 4-PPBP or a salt thereof (e.g., 4-PPBP maleate), and a pharmaceutically acceptable excipient: and administering the composition to the connective tissue defect of the subject; wherein the connective tissue defect is a tendon injury or a ligament injury. In certain embodiments the connective tissue defect is a tendon injury, for example a patellar tendon injury, an Achilles tendon injury, a rotator cuff injury, or lateral epicondylitis. In some embodiments the composition further includes a matrix material, a surgical adhesive, or a fibrin glue. In additional embodiments the composition or pharmaceutical composition further includes an antibiotic, an anti-inflammatory, a cytokine, a growth factor, or a stem cell. In still other embodiments the Oxo M and said 4-PPBP are encapsulated in a microsphere. In particular embodiments the subject is a human subject.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A-1F is a series of bar graphs showing tendon-related gene expressions in CD146+ perivascular tendon stem/progenitor cells (PTSCs) when treated by selected small molecules. At 1 week of treatment, 4-PPBP significantly increased COL-I (FIG. 1A) and COL-III (FIG. 1B), whereas Oxo-M significantly increased Tn-C (FIG. 1C), VIM (FIG. 1D), and Scx (FIG. 1F) (*: $p<0.05$ compared to control). Oxo-M: Oxotremorine M (1 mM), PAO: Phenylarsine oxide (2 µM), 4-PPBP: PPBP maleate (10 µM), BOM: [Tyr4]-Bombesin (10 nM).

FIG. 4A-4H is a series of H&E stained slides showing healing of fully transected rat patellar tendons by small molecules. At 1 week post-op, delivery of Oxo-M (1 mM)+4-PPBP (10 µM) resulted in reduced gaps and more aligned collagen structure (FIG. 4D), as compared to disorganized scar-like tissue with control (FIG. 4A), Oxo-M alone (FIG. 4B), and 4-PPBP alone (FIG. 4C). At 2 weeks post-op, control (FIG. 4E), Oxo-M alone (FIG. 4F), and 4-PPBP alone (FIG. 4G) groups ended up with scar-like healing, whereas Oxo-M+4-PPBP (FIG. 4H) showed significantly improved healing with densely aligned fibers.

FIG. 6A-6H shows polarized image of Picrosirius Red (PR) stained slides. Delivery of Oxo-M (1 mM)+4-PPBP (10 µM) showed re-organized collagen fibers by 1 week post-op (FIG. 6D) and 2 weeks post-op (FIG. 6H) as compared to disrupted collagen structure at 1 week and 2 weeks post-op with control (FIG. 6A and FIG. 6E, respectively), Oxo-M alone (FIG. 6B and FIG. 6F, respectively), and 4-PPBPalone (FIG. 6C and FIG. 6G, respectively) delivered groups.

FIG. 7A-7D shows immunofluorescence for CD146 and COL-I in tendon healing by control (FIG. 7A), Oxo-M alone (FIG. 7B), 4-PPBP alone (FIG. 7C) and a combination of Oxo-M and 4-PPBP (FIG. 7D) at 1 week post-op.

DETAILED DESCRIPTION OF THE INVENTION

Figure 1C:
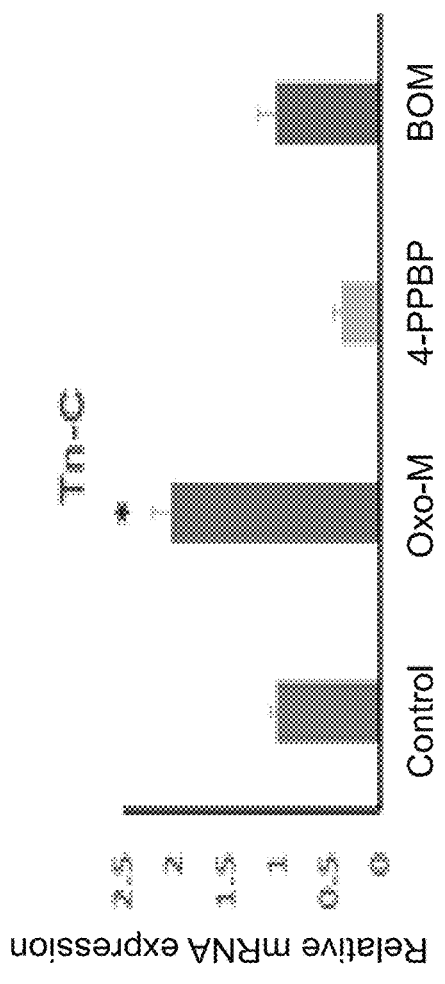
Figure 1D:
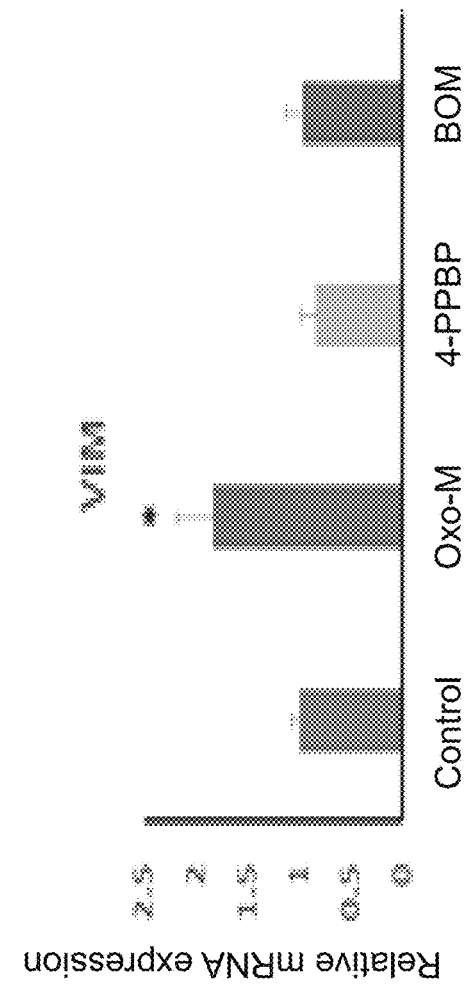
Figure 2A:
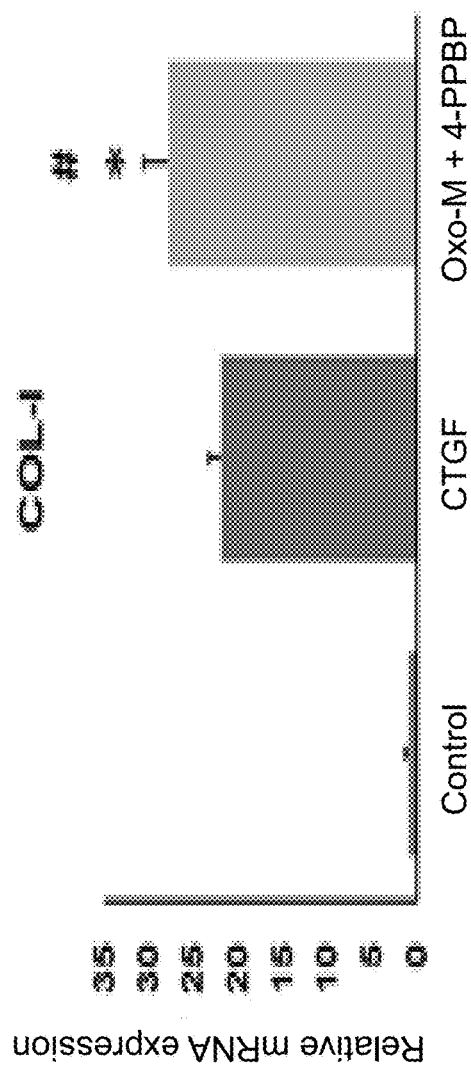
FIG. 2A-2F is series of bar graphs showing tendon-related gene expressions in CD146+ perivascular tendon stem/progenitor cells (PTSCs) when treated by Oxo-M+4-PPBP. At 1 week of treatment, Oxo-M+4-PPBP significantly increased expressions of COL-I (FIG. 2A), III (FIG. 2B), Tn-C (FIG. 2C), VIM (FIG. 2D), TnmD (FIG. 2E), and Scx (FIG. 2F), at a similar or higher level of CTGF (*: $p<0.05$ compared to control; #: $p<0.05$ compared to 100 ng/mL CTGF).
Figure 2B:
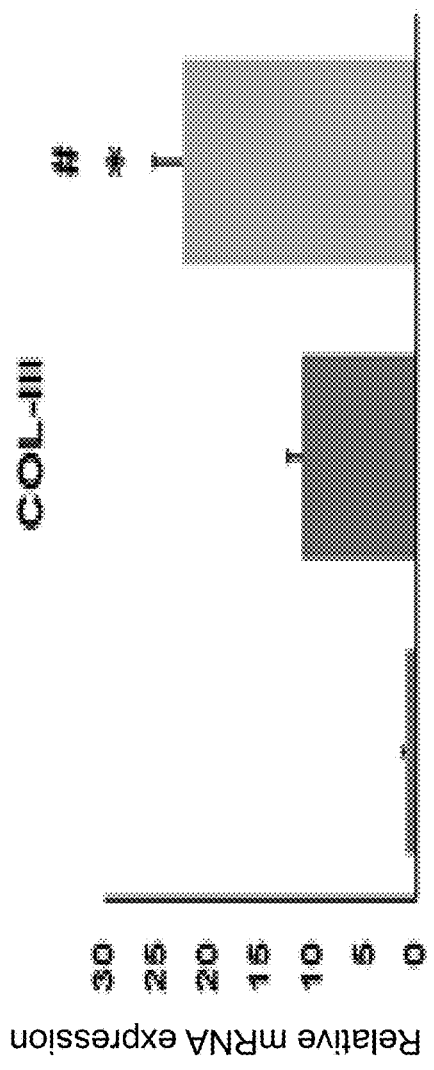
Figure 2C:
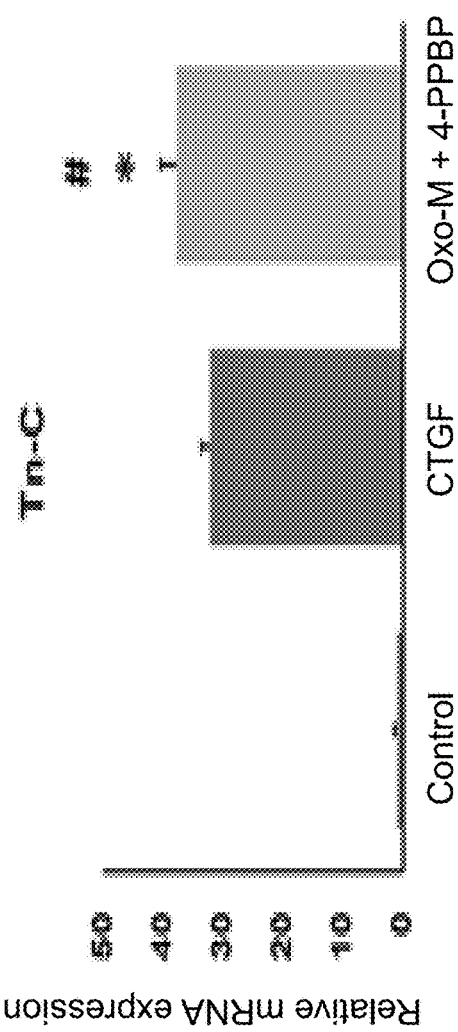
Figure 2D:
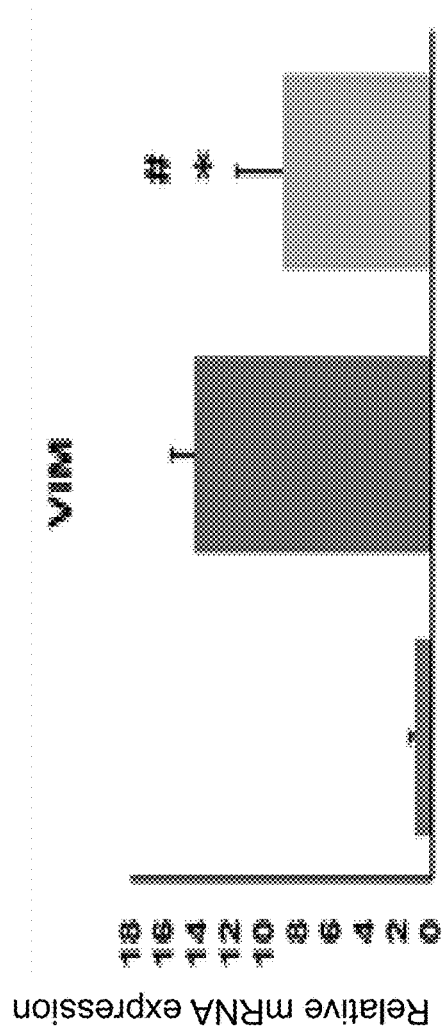
Figure 2E:
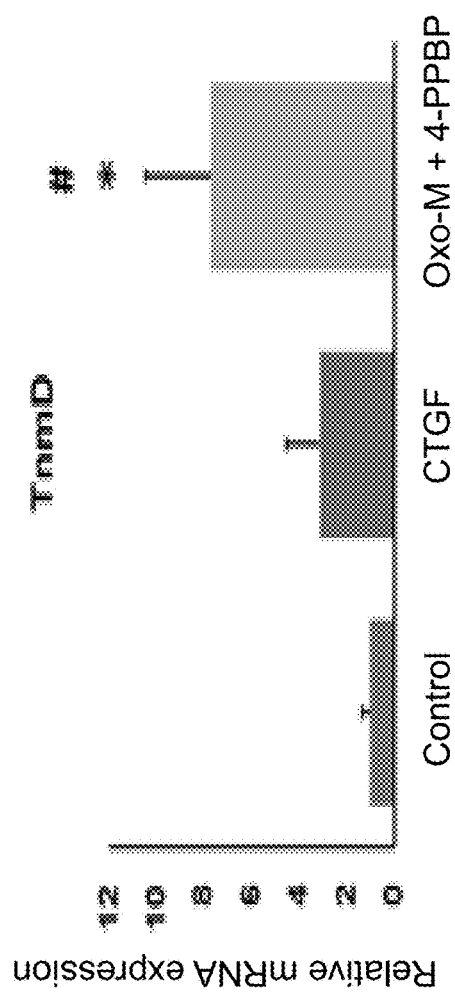
Figure 2F:
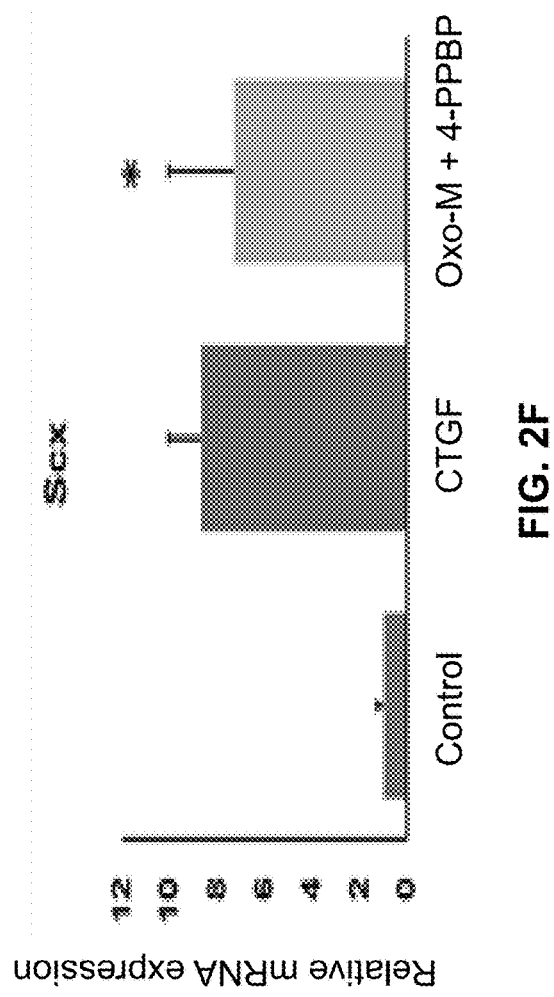

The present disclosure is based, at least in part, on the discovery that a combination of oxotremorine M (Oxo-M) and PPBP (4-PPBP maleate) induces tenogenic differentiation of perivascular tendon stem cells. The combination of Oxo-M and 4-PPBP, which has been shown to induce differentiation of PTSCs into tendon-like cells, can be used as a therapy for healing or regenerating tendon injury or ligament injury.

As shown herein, healing, repair, or regeneration can be achieved by recruiting, activating, or differentiating either tissue-resident or circulating stem cells, instead of stem cell transplantation necessitating ex vivo manipulation. Regeneration by harnessing the regenerative potential of endogenous stem cells can serve as a straightforward strategy for regenerative medicine that can overcome the current translational hurdles associated with cell transplantation. Thus is provided a breakthrough in treatment of injured or degenerated tissues, tendon, or ligament.

This discovery provides for use of small molecule chemical compounds as an alternative or supplement to conventional growth factor approaches for induction of tenogenic differentiation of tendon stem cells and related compositions and methods for tendon and ligament healing or regeneration.

As shown herein, a combination of two small molecule chemical compounds, Oxotremorine M (Oxo-M) and PPBP maleate (4-PPBP) induces the tenogenic differentiation of CD146+ perivascular tendon stem/progenitor cells (PTSCs) with a similar or higher level of efficiency compared to CTGF. First tested were several selected FAK or ERK1/2 agonists, including Oxo-M, 4-PPBP, Phenylarsine oxide (PAO), and [Tyr4]-Bombesin (BOM), to cultured rat PTSCs. Results described herein showed that after 1 week in vitro, only Oxo-M (1 mM) and 4-PPBP (10 µM) resulted in 1.5-2.5 fold increase in tendon-related gene expressions, including collagen I and III, tenascin-C (Tn-C), vimentin (VIM), tenomodulin (Tnmd), and scleraxis (Scx). Further experiments showed when Oxo-M (1 mM) and 4-PPBP (10 µM) were applied together, the tendon-related gene expressions were dramatically increased up to about 6-40 fold at a similar level achieved by CTGF. These findings show that Oxo-M and 4-PPBP have synergetic effects to induce tenogenic differentiation of the specific population of tendon stem/progenitor cells. It was previously shown that stimulation of tenogenic differentiation of PTSCs is a key to regenerate torn tendons (see, e.g., Lee, et al., 2015, supra). New findings that a combination of Oxo-M and 4-PPBP dramatically increase (e.g., synergistically increase) tendon-related gene expressions provides effective therapeutic compositions and methods for treatment of tendon injuries.

In some embodiments, Oxo-M and 4-PPBP each induce expression of tendon-related markers in PTSCs. In some embodiments, the synergistic combination of Oxo-M and 4-PPBP can further increase expression of key tendon markers to comparable or higher levels than CTGF stimulation. This combination of Oxo-M and 4-PPBP can be used as a small molecule-based therapeutic for stem cell-mediated repair of tendon and ligament injuries.

The combination of chemical compounds described herein can provide a better route of administration or well-controlled outcome.

One embodiment of the present disclosure provides a pharmaceutical composition for treating tendon or ligament injury in a subject (e.g., an animal or human). One embodiment of the present disclosure provides a pharmaceutical composition for incorporation into a graft or patch to promote tendon healing in in a subject. One embodiment of the present disclosure provides for generation of tenocytes from stem cells for tendon tissue engineering. One embodiment of the present disclosure provides a tool to study molecular mechanisms of tenogenesis and tendon development.

Oxo-M

Oxotremorine (CAS No. 70-22-4; ChEMBL7634; $C_{12}H_{18}N_2O$) has the following structure:

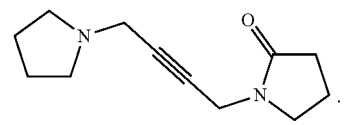 [SMILES: O=C1CCCN1CC#CCN1CCCC1]

Oxotremorine is also known as 1-(4-[1-Pyrrolidinyl]-2-butynyl)-2-pyrrolidinone; 1-(4-[1-Pyrrolidinyl]2-butynyl)-2-pyrrolidinone; or 1-(4-Pyrrolidin-1-ylbut-2-yn-1-yl)pyrrolidin-2-one.

Oxotremorine is available as a salt. Oxotremorine methiodide (Oxo-M) is the iodine salt of Oxo.

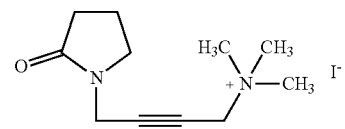

Oxotremorine sesquifumarate salt has the following structure:

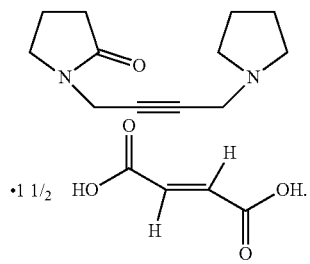

Oxotremorine and salts thereof are commercially available (see, e.g., Tocris Bioscience; Sigma-Aldrich).

The present disclosure refers to Oxo-M but it is understood that such recitation can refer to oxotremorine or another salt form of oxotremorine.

4-PPBP

PPBP (4-PPBP) (CAS Number 136534-70-8; 4-phenyl-1-(4-phenylbutyl) piperidine; $C_{21}H_{27}N$) has the following structure:

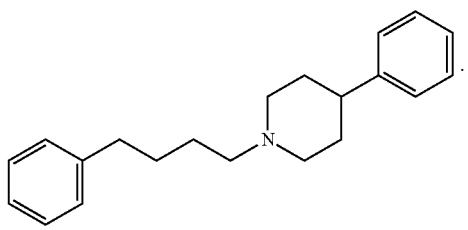 [SMILES: c1ccc(CCCCN2CCC(c3ccccc3)CC2)cc1]

PPBP maleate (4-PPBP maleate) (CAS Number 207572-62-1; 4-phenyl-1-(4-phenylbutyl)-piperidine maleate; $C_{21}H_{27}N \cdot C_4H_4O_4$) has the following structures:

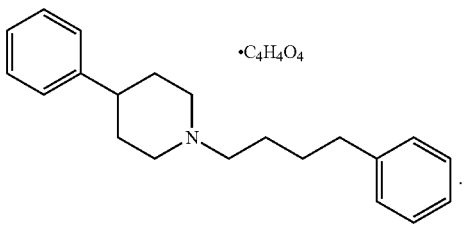

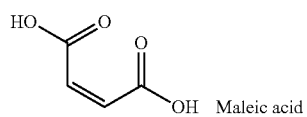
Maleic acid

Maleate ion.

with salt.

with salt.

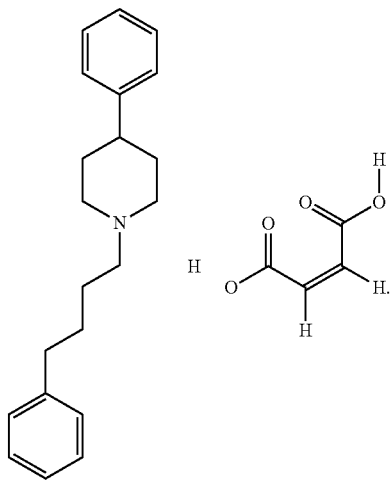

Maleate is the ionized (i.e., deprotonated) form of maleic acid and will have a negative charge. In the diagram below, X is understood as a halogen salt (e.g., NaCl, CaCl$_2$ or a similar salt).

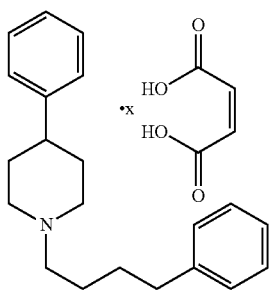

The pH can be adjusted to deprotonate. The pKa of maleic acid is 2, which is low enough to where it would easily give up a proton to a base (e.g., NaOH, Ca(OH)$_2$)

PPBP maleate is commercially available (see, e.g., Tocris Bioscience; Sigma-Aldrich; Santa Crux Biotech).

The present disclosure refers to 4-PPBP but it is understood that such recitation can refer to 4-PPBP or 4-PPBP maleate or another salt form.

Kartogenin

Kartogenin has the following structure:

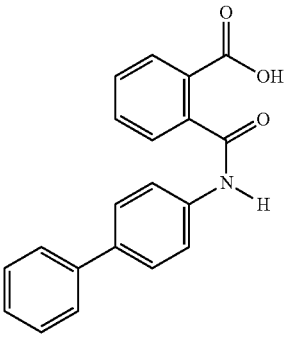 [SMILES: O=C(O)c1ccccc1C(=O)Nc1ccc(-c2ccccc2)cc1]

Kartogenin is available from Stem Cell Technologies (Cat #72572). The present disclosure refers to Kartogenin but it is understood that such recitation can refer to kartogenin or a salt form thereof.

Icariin

Icariin has the following structure:

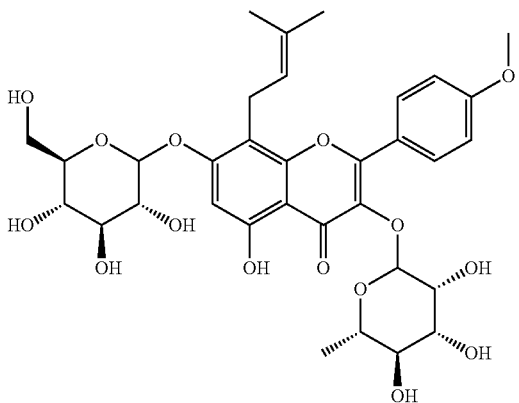 [SMILES: COc1ccc(-c2oc3c(CC=C(C)C)c(OC4O[C@H](CO)[C@@H](O)[C@H](O)[C@H]4O)cc(O)c3c(=O)c2OC2O[C@@H](C)[C@H](O)[C@@H](O)[C@H]2O)cc1]

Icariin is available from multiple sources including Live-Long Nutrition (Cat # B004579RJY). The present disclosure refers to icariin but it is understood that such recitation can refer to icariin or a salt form thereof.

Progenitor Cells

A progenitor cell, as that term is used herein, is a precursor to a fibrochondrocyte or fibrochondrocyte-like cell and can differentiate in the presence of CTGF or a composition described herein. A progenitor cell can be a multipotent cell. A progenitor cell can be self-renewing. For example, a progenitor cell can be a mesenchymal stem cell (e.g., a human mesenchymal stem cell). The progenitor cell can be substantially less differentiated than a fibrochondrocyte or fibrochondrocyte-like cell. The progenitor cell can be a perivascular tendon stem/progenitor cell (PTSC). The progenitor cell can be a CD146+ perivascular tendon stem/progenitor cell.

Chemistry

The following definitions and methods are provided to better define the present disclosure and to guide those of ordinary skill in the art in the practice of the present disclosure. Unless otherwise noted, terms are to be understood according to conventional usage by those of ordinary skill in the relevant art.

A chemical bond is understood as an attraction between atoms of a biomolecule and atoms of a matrix material that allows the formation of a linkage between atoms (e.g., atoms of the same molecule or different molecules). A bond can be caused by an electrostatic force of attraction between opposite charges, either between electrons and nuclei, or as the result of a dipole attraction. A bond can be, for example, a covalent bond, a coordinate covalent bond, an ionic bond, polar covalent, a dipole-dipole interaction, a London dispersion force, a cation-pi interaction, or hydrogen bonding.

Encapsulation

As described herein, an active agent can be encapsulated in a microsphere (μS). Such microspheres are useful as slow release compositions. For example, small molecules such as Oxo-M,4-PPBP, kartogenin and/or icariin can be microencapsulated to provide for enhanced stability or prolonged delivery. Encapsulation vehicles include, but are not limited to, microparticles, liposomes, microspheres, or the like, or a combination of any of the above to provide the desired release profile in varying proportions. Other methods of controlled-release delivery of agents will be known to the skilled artisan. Moreover, these and other systems can be combined or modified to optimize the integration/release of agents. For example, the agents encapsulated in the microspheres can have a total accumulated release rate of from about 0% to about 50% over the course of at least 42 days. It is understood that recitation of the above range includes discrete values between the recited range. One skilled in the art will understand that the distribution of release rate can have any distribution including a normal distribution or a non-normal distribution.

For example, the polymeric delivery system can be a polymeric microsphere, e.g., a PLGA polymeric microsphere. A variety of polymeric delivery systems, as well as methods for encapsulating a molecule such as a growth factor, are known to the art (see, e.g., Varde and Pack, *Expert Opin. Biol. Ther.* 4:35-51, 2004). Polymeric microspheres can be produced using naturally occurring or synthetic polymers and are particulate systems in the size range of 0.01 to 500 μm. Polymeric microspheres can have a mean diameter of about 0.01 μm, about 0.05 μm, about 0.1 μm, about 0.5 μm, about 1 μm, 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, or about 500 μm, or more.

Polymeric micelles and polymeromes are polymeric delivery vehicles with similar characteristics to microspheres and can also facilitate encapsulation and matrix integration of the compounds described herein. Fabrication, encapsulation, and stabilization of microspheres for a variety of payloads are within the skill of the art (see, e.g., Varde and Pack, 2004, supra). The release rate of the microspheres can be tailored by type of polymer, polymer molecular weight, copolymer composition, excipients added to the microsphere formulation, and microsphere size. Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and/or oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme).

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as an animal or a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc., Rockville, Md., 2005 ("USP/NF"), or a more recent edition, and the components listed in the continuously updated Inactive Ingredient Search online database of the FDA. Other useful components that are not described in the USP/NF, etc., may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating connective tissue defect (e.g., tendon injury or ligament injury) in a subject in need thereof by administration of a therapeutically effective amount of a composition including Oxo-M and 4-PPBP, and optionally kartogenin or icariin, or both so as to heal, repair, or regenerate the tendon or ligament. Another process of treating connective tissue involves administering a therapeutically effective amount of Oxo-M, 4PPBP, kartogenin or icariin, or a combination thereof, in a matrix material or scaffold.

Methods described herein are generally performed on a subject in need thereof. A subject in need of the therapeutic methods described herein can be a subject having, diagnosed with, suspected of having, or at risk for developing tendon injury or ligament injury. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a composition including Oxo-M and 4-PPBP, and optionally kartogenin or icariin, or both, is, for example, that amount that would cause the desired therapeutic effect in a subject while minimizing undesired side effects. In various embodiments, an effective amount of a composition including Oxo-M and 4-PPBP described herein can recruit PTSCs; induce tenogenic differentiation of tendon stem cells, increase (e.g., synergistically increase) tenogenic differentiation and increases expression of tenogenic markers collagen I and II, vimentin, tenomodulin, and scleraxis in PTSCs (e.g., to comparable or higher levels than CTGF stimulation); or heal, repair, or regenerate tendon or ligament defects.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a composition including Oxo-M and 4-PPBP and optionally kartogenin or icariin, or both, can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to recruit PTSCs; induce tenogenic differentiation of tendon stem cells, increase (e.g., synergistically increase) tenogenic differentiation and increases expression of tenogenic markers collagen I and II, vimentin, tenomodulin, and scleraxis in PTSCs (e.g., to comparable or higher levels than CTGF stimulation); or heal, repair, or regenerate tendon or ligament defects.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Shawl (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Treatment in accord with the methods described herein can be performed prior to, concurrent with, or after conventional treatment modalities for connective tissue defects, such as tendon or ligament injuries.

A composition including Oxo-M and 4-PPBP can be administered simultaneously or sequentially with another agent, such as an antibiotic, an anti-inflammatory, or another agent, or in certain embodiments a cytokine, a growth factor, or even a stem cell. For example, a composition including Oxo-M and 4-PPBP can be administered simultaneously with another agent, such as an antibiotic or an anti-inflammatory. Simultaneous administration can occur through administration of separate compositions, each containing one or more of a Oxo-M and 4-PPBP, an antibiotic, an anti-inflammatory, or another agent. Simultaneous administration can occur through administration of one composition containing two or more of Oxo-M and 4-PPBP, an antibiotic, an anti-inflammatory, or another agent. A composition including Oxo-M and 4-PPBP can be administered sequentially with an antibiotic, an anti-inflammatory, or another agent. For example, a composition including Oxo-M and 4-PPBP can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

Administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

In some embodiments, Oxo-M, 4PPBP, kartogenin or icariin, or combination thereof, can be mixed with a matrix material (e.g., a surgical adhesive), and optionally include a visualizing agent as described below. For example, Oxo-M or 4PPBP can be mixed with a fibrin glue, an iCMBA, BioGlue® (e.g., a mix of purified bovine serum albumin (BSA) and glutaraldehyde), or a malonic acid derivative.

A composition described herein can be administered via a scaffold comprising a matrix material. In some embodiments, the scaffold can include an endogenous or exogenous cell introduced to the scaffold ex vivo or in vivo. In some embodiments, the scaffold includes an endogenous progenitor cell. In some embodiments, the scaffold does not include an exogenous progenitor cell. In some embodiments, the scaffold includes progenitor cell prior to scaffold delivery to the tissue defect site. In some embodiments, the scaffold does not include a progenitor cell until after scaffold delivery to the tissue defect site. In some embodiments, the scaffold includes an endogenous progenitor cell introduced to the scaffold in vivo or ex vivo. In some embodiments, the scaffold includes an exogenous progenitor cell introduced to the scaffold in vivo or ex vivo. Features related to cells in the scaffold can be combined with other features discussed herein.

In some embodiments, the tissue defect site is at least partially located in an inner or avascular region of a cartilaginous tissue. In some embodiments, the tissue defect includes a tear, injury, osteoarthritis, or degeneration. In some embodiments, the tissue defect includes a longitudinal or vertical tear, a radial tear, a horizontal tear, a bucket handle tear, a parrot beak tear, or a flap tear. In some embodiments, the tissue (in which the defect is present) can be cartilaginous tissue, cartilage, a meniscus, a knee meniscus, a ligament, a ligament enthesis, a tendon, a tendon enthesis, an intervertebral disc, a temporomandibular joint (TMJ), a TMJ ligament, or a triangular fibrocartilage. Features related to tissue and tissue defect can be combined with other features discussed above and below.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow co-localized deposition with other agents or excipients; improve the stability of the agent in vivo; prolong the residence time of the agent at its site of action by reducing clearance; decrease the nonspecific delivery of the agent to non-target tissues; decrease irritation caused by the agent; decrease toxicity due to high initial doses of the agent; alter the immunogenicity of the agent; decrease dosage frequency, improve taste of the product; or improve shelf life of the product.

Scaffold Fabrication and Related Embodiments

According to certain embodiments, provided are scaffolds and methods of making scaffolds that incorporate encapsulated Oxo-M, 4-PPBP, kartogenin or Icariin, or any combination thereof. One example is the implementation of microspheres encapsulating one or more of the foregoing agents and combining them with a matrix material that is suitable for forming a scaffold via 3D printing. A scaffold can then be engineered using this combination of materials. US. Patent Pub. US2018/0085493 provides supporting disclosure for matrix materials, scaffolds produced via 3D printing, polymeric fibers, and methods of fabrication, among other information. PCT Pub WO/2016/149153 provides supporting disclosure on methods of treating tissue defects that involve scaffolds that comprise releasable factors that promote migration and proliferation of cells. Such publications are incorporated herein by reference for support of 3D printing techniques and scaffold formation.

A 3D printing device can include one or more cartridges for containing a matrix material, microencapsulated active agent, or various combinations thereof. A 3D printing device can include one or more cartridges active concurrently or sequentially. A 3D printing device can include a plurality of cartridges active concurrently or sequentially. A 3D printing device can include a first plurality of cartridges and a second plurality of cartridges active concurrently or sequentially. For example, formation of a 3D printed scaffold described herein can include a plurality of cartridges, each containing independently selected matrix material, microencapsulated active agent, or various combinations thereof. For example, formation of a 3D printed scaffold described herein can include 1, 2, 3, 4, 5 6, 7, 8, 9, 10, or more cartridges, each containing independently selected matrix material, microencapsulated active agent, or various combinations thereof. Multiple cartridges can share or have independent elements such as a heating element or printing needle. For example, multiple cartridges can each contain an independent heating element (e.g., having same or different temperature or melting profiles) or printing needle (e.g., having same or different inner diameter). A 3D printing device can switch cartridges before, during or after polymeric microfiber formation or scaffold formation. For example, printing cartridges containing the same or different matrix materials or microencapsulated active agents or printing needle size can be switched during fabrication of a polymeric microfibril or during fabrication of a layer, region, or other structure of the scaffold so as to provide, e.g., differing spatial compositions of matrix and active agent. As another example, printing cartridges containing the same or different matrix materials or microencapsulated active agents or printing needle size can be switched to control temperature of the microencapsulated active agents, e.g., to maintain the microencapsulated active agents below a threshold temperature (as further described herein).

According to one embodiment, provided is a method of forming a biocompatible scaffold. The method involves one or more steps of (i) encapsulating at least one agent in a plurality of microspheres; (ii) combining the plurality of microspheres and a matrix material, the matrix material being suitable for forming a scaffold via 3D printing; (iii) introducing the combination of microspheres and matrix material into a first cartridge of a 3D printing device; (iv) heating the combination of microspheres and matrix material in the first cartridge sufficiently to allow dispensing of the combination while preventing substantial degradation of the microsphere or the at least one agent encapsulated in the microsphere; (v) dispensing the heated combination of microspheres and matrix material from the first cartridge through a printing needle to form a polymeric microfiber, wherein the microspheres are distributed through the polymeric microfiber; and (vi) forming a scaffold comprising a plurality of the polymeric microfibers, wherein the microspheres are distributed through the scaffold by way of the polymeric microfibers.

Another embodiment pertains to a method of forming a polymeric fiber having a microencapsulated agent distributed in the polymeric fiber. This method embodiment involves one or more steps of: (i) encapsulating at least one agent in a plurality of microspheres; (ii) combining the plurality of microspheres and a matrix material, the matrix material being suitable for forming a scaffold via 3D printing; (iii) introducing the combination of microspheres and matrix material into a first cartridge of a 3D printing device; (iv) heating the combination of microspheres and matrix material in the first cartridge sufficiently to allow dispensing of the combination of microspheres and matrix material while preventing substantial degradation of the microsphere or the agent encapsulated in the microsphere; and (v) dispensing the heated combination of microspheres and matrix material from the cartridge through a printing needle to form a polymeric microfiber, wherein the microspheres are distributed through the polymeric microfiber.

The methods described above may further comprise introducing the combination of microspheres and matrix material into a second cartridge of a 3D printing device; heating the combination of microspheres and matrix material in the second cartridge sufficiently to allow dispensing of the combination of microspheres and matrix material while preventing substantial degradation of the microsphere or the agent encapsulated in the microsphere; and interchanging the first cartridge and the second cartridge during a printing process.

The at least one agent that is encapsulated in the microspheres includes Oxo-M, 4-PPBP, kartogenin or Icariin, or any combination thereof.

Embodiments disclosed herein include microfibers produced by the methods above as well as scaffolds made of a plurality of microfibers.

Embodiments of the present invention involve implanting scaffolds as taught herein. Typically, the scaffolds implanted to treat a tissue defect in a subject in need. Tissue defects treated may be associated with a multi-tissue interface. Examples of multi-tissue interfaces include, but are not limited to, musculoskeletal system; craniofacial system; periodontium; cementum (CM)-periodontal ligament (PDL)-alveolar bone (AB) complex; ligament-to-bone insertion; tendon-to-bone insertion; rotator cuff; supraspinatus tendon-to-bone interface; interface between tendon, fibrocartilage, or bone; supraspinatus tendon-fibrocartilage-bone interface; articular cartilage-to-bone junction; anterior cruciate ligament (ACL)-to-bone complex; anterior cruciate ligament-fibrocartilage-bone interface; intervertebral disc; nucleus pulposus-annulus fibrosus-endplates; cementum-periodontal ligament-alveolar bone; muscle-to-tendon; inhomogeneous or anisotropic tissues; knee meniscus; temporomandibular joint disc; periodontium; root-periodontium complex; synovial joints; or fibrocartilaginous tissues.

Figure 15:
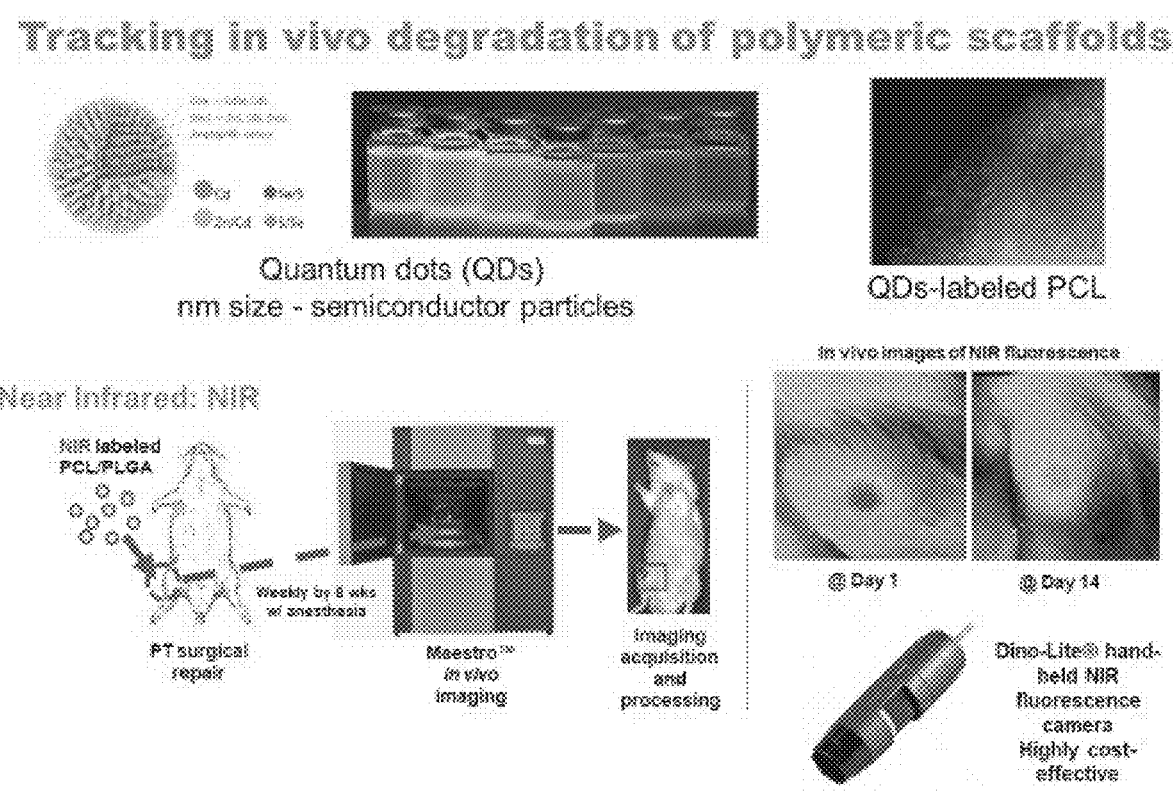
FIG. 15 is a series of images showing the implementation of visual agents (e.g. quantum dots) that allow for the tracking of in vivo degradation of implanted polymeric scaffolds.
Figure 16:
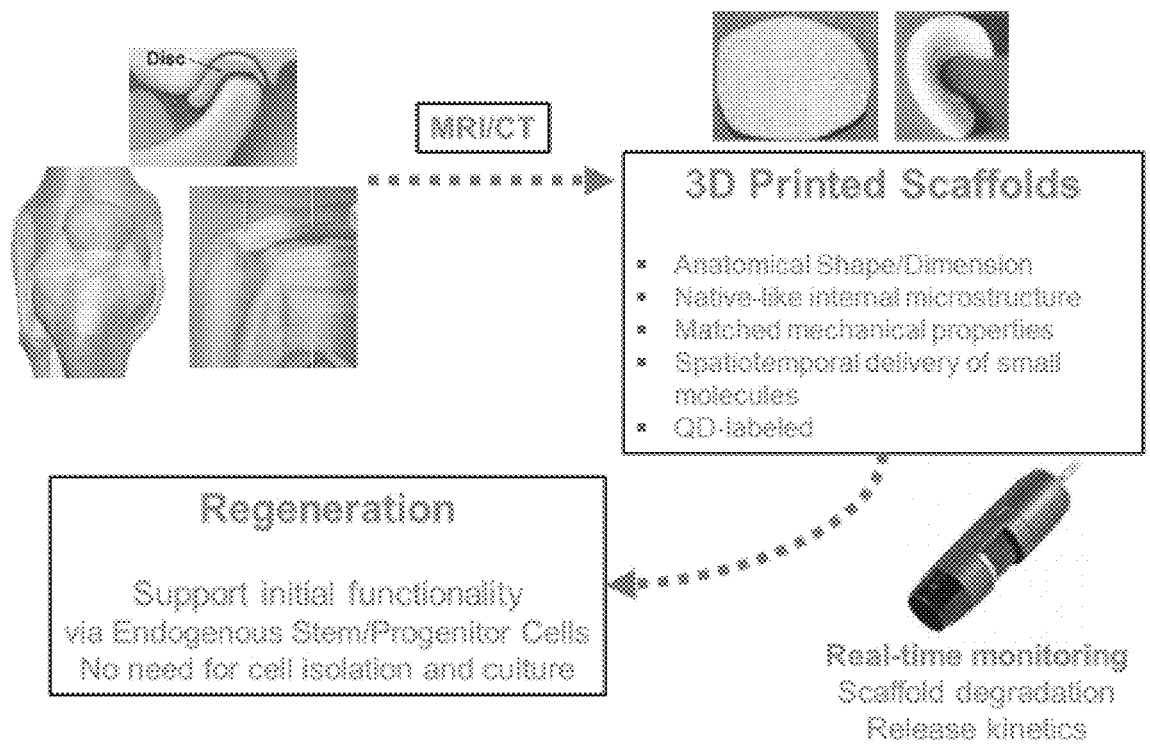
FIG. 16 is a series of images that show 3D printed scaffolds that possess anatomical shape/dimension of tissues, native-like internal microstructures with matched mechanical properties, provide for spatiotemporal delivery of small molecules (e.g. Oxo-M, 4-PPBP, kartogenin and icariin), and labeled with a visual agent (e.g. quantum dots). The scaffold can be visualized with near infrared imaging.

In another embodiment, the material provided in any of the cartridges of the 3D printing device includes a visualizing agent. Examples of visualizing agents include fluorescent molecular probes (e.g. ProSense750, Perkin Elmer; IRDye® 800CW 2-DG, LiCor Biosciences), quantum dots and near-infrared molecular probes, and the like. This will enable the monitoring in vivo degradation of scaffolds made upon their implantation into a subject. For example, the visualization agent includes quantum dots that become embedded into the scaffold. Upon implantation into the subject the degradation of the scaffold can be monitored by imaging techniques such as near-infrared imaging, see FIGS. 15 and 16. Other examples would include fluorescent molecular probes that can be detected by fluorescence reflectance imaging.

Screening

Also provided are methods for screening.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 molecular weight (MW), or less than about 1000 MW, or less than about 800 MW) organic molecules or inorganic molecules, including, but not limited to, salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

Candidate molecules can be derivatives of Oxo-M. Candidate molecules can be derivatives of 4-PPBP.

A candidate molecule can be a compound in a library database of compounds. One of skill in the art will be generally familiar with, for example, numerous databases for commercially available compounds for screening (see, e.g., ZINC database, UCSF, with 2.7 million compounds over 12 distinct subsets of molecules; Irwin and Shoichet, *J. Chem. Inf. Model* 45:177-182, 2005). One of skill in the art will also be familiar with a variety of search engines to identify commercial sources or desirable compounds and classes of compounds for further testing (see, e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see, e.g., Lipinski, *J. Pharmacol. Toxicol. Methods* 44:235-249, 2000). Initial screening can be performed with lead-like compounds.

When designing a lead from spatial orientation data, it can be useful to understand that certain molecular structures are characterized as being "drug-like." Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to Oxo-M and 4-PPBP, and optionally kartogenin and icariin. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

Compositions and methods described herein utilizing molecular biology protocols can be according to a variety of standard techniques known to the art (see, e.g., Sambrook and Russel (2006) *Condensed Protocols from Molecular Cloning: A Laboratory Manual*, Cold Spring Harbor Laboratory Press, ISBN-10: 0879697717; Ausubel, et al. (2002) *Short Protocols in Molecular Biology*, 5th ed., Current Protocols, ISBN-10: 0471250929; Sambrook and Russel (2001) *Molecular Cloning: A Laboratory Manual*, 3d ed., Cold Spring Harbor Laboratory Press, ISBN-10: 0879695773; Green and Sambrook 2012 *Molecular Cloning: A Laboratory Manual*, 4th ed., Cold Spring Harbor Laboratory Press, ISBN-10: 1605500569; Elhai and Wolk, *Methods Enzymol.* 167:747-754, 1988; Studier, *Protein Expr. Purif.* 41:207-234, 2005; Gellissen, ed. (2005) *Production of Recombinant Proteins: Novel Microbial and Eukaryotic Expression Systems*, Wiley-VCH, ISBN-10: 3527310363; Baneyx (2004) *Protein Expression Technologies*, Taylor & Francis, ISBN-10: 0954523253).

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

As used herein, substantially, when used as a modifier of a term, refers to a state in which the functional properties of the term are not influenced beyond a normal tolerance permitted by one skilled in the art. Thus, a first compound or composition that is substantially free of a second compound or composition refers to a first compound or composition whose functional properties are not influenced by the second compound or composition beyond normal tolerance permitted by one skilled in the art.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All references cited herein are incorporated by reference in their entireties for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

The following example shows a combination of Oxo-M and 4-PPBP induces tenogenic differentiation of perivascular tendon stem cells.

Perivascular tendon stem cells (PTSCs) were isolated from patellar tendons of 12 week-old Sprague-Dawley rats by sorting cells with strong surface expression of CD146, following established protocol (Lee, et al., 2015, supra). Culture-expanded PTSC (P2-3) were then treated with selected FAK and ERK1/2 agonists, including Oxotremorine M (Oxo-M) (1 mM), PPBP maleate (4-PPBP) (10 µM), Phenylarsine oxide (PAO) (2 µM), and [Tyr4]-Bombesin (BOM) (10 nM), and SKF-83959 (20 µM). A single concentration was tested for each molecule as a first screening study. After 1 week, tendon-related mRNA expressions, including collagen I and III, tenascin-C (Tn-C), vimentin (VIM), tenomodulin (Tnmd), and scleraxis (Scx), were measured.

Results showed that Oxo-M provided significant increases in Tn-C, VIM, and Scx, while 4-PPBP elevated expressions of COL-I and COL-III (FIG. 1A-F). When a combination of Oxo-M and 4-PPBP were applied together, the tendon-related gene expressions were dramatically increased up to ~6-40 fold at a similar level achieved by CTGF (FIG. 2A-F).

Other tested FAK and ERK1/2 agonists either did not affect gene expression or significantly lowered cell viability. BOM and PAO failed to affect the gene expressions. SKF-83959 significantly lowered cell viability.

These findings show that Oxo-M and 4-PPBP have synergetic effects to induce tenogenic differentiation of the specific population of tendon stem/progenitor cells. These findings also show that not all FAK and ERK1/2 agonists necessarily share these properties.

Figure 3A:
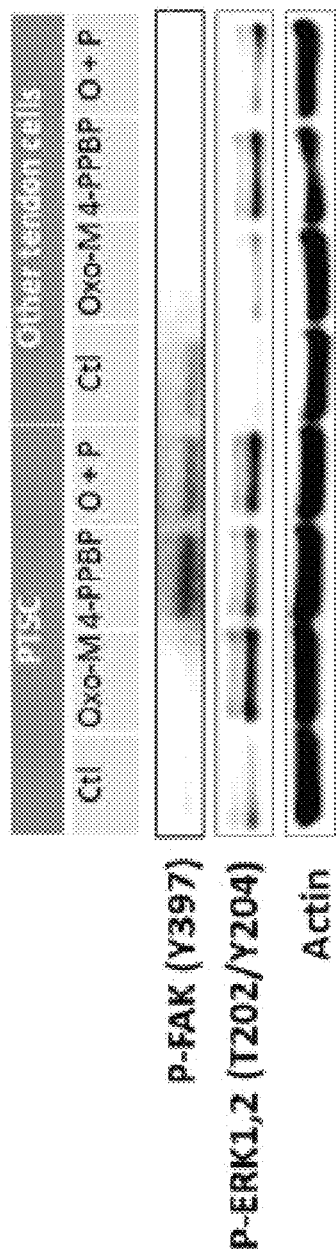
FIG. 3A and FIG. 3B are a Western Blot showing phosphorylation of FAK and ERK1/2 induced by Oxo-M and 4-PPBP (FIG. 3A) and siRNA knockdown of FAK and ERK1/2 significantly reduced Scx expression induced by Oxo-M and 4-PPBP (FIG. 3B). n=5 per group; *: $p<0.05$ compared to all the other groups.
Figure 3B:
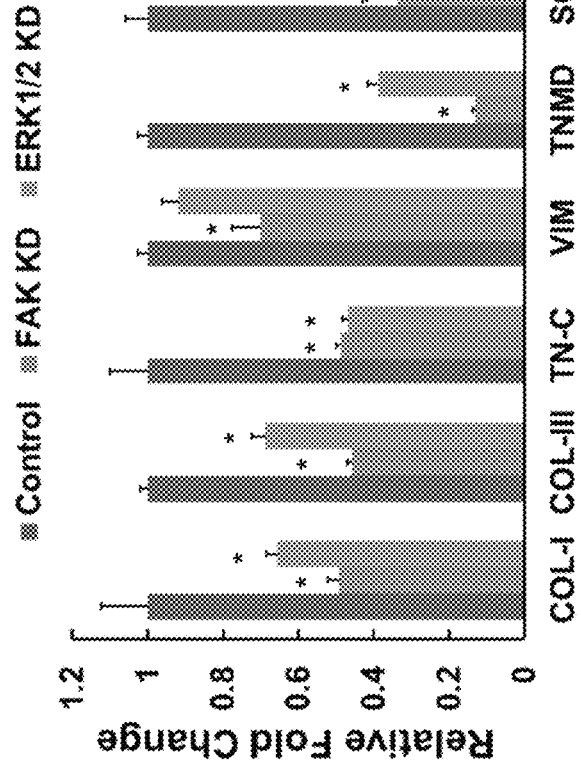
Figures 5A, 5B, 5C, 5D, 5E, 5F, 5G, 5H:
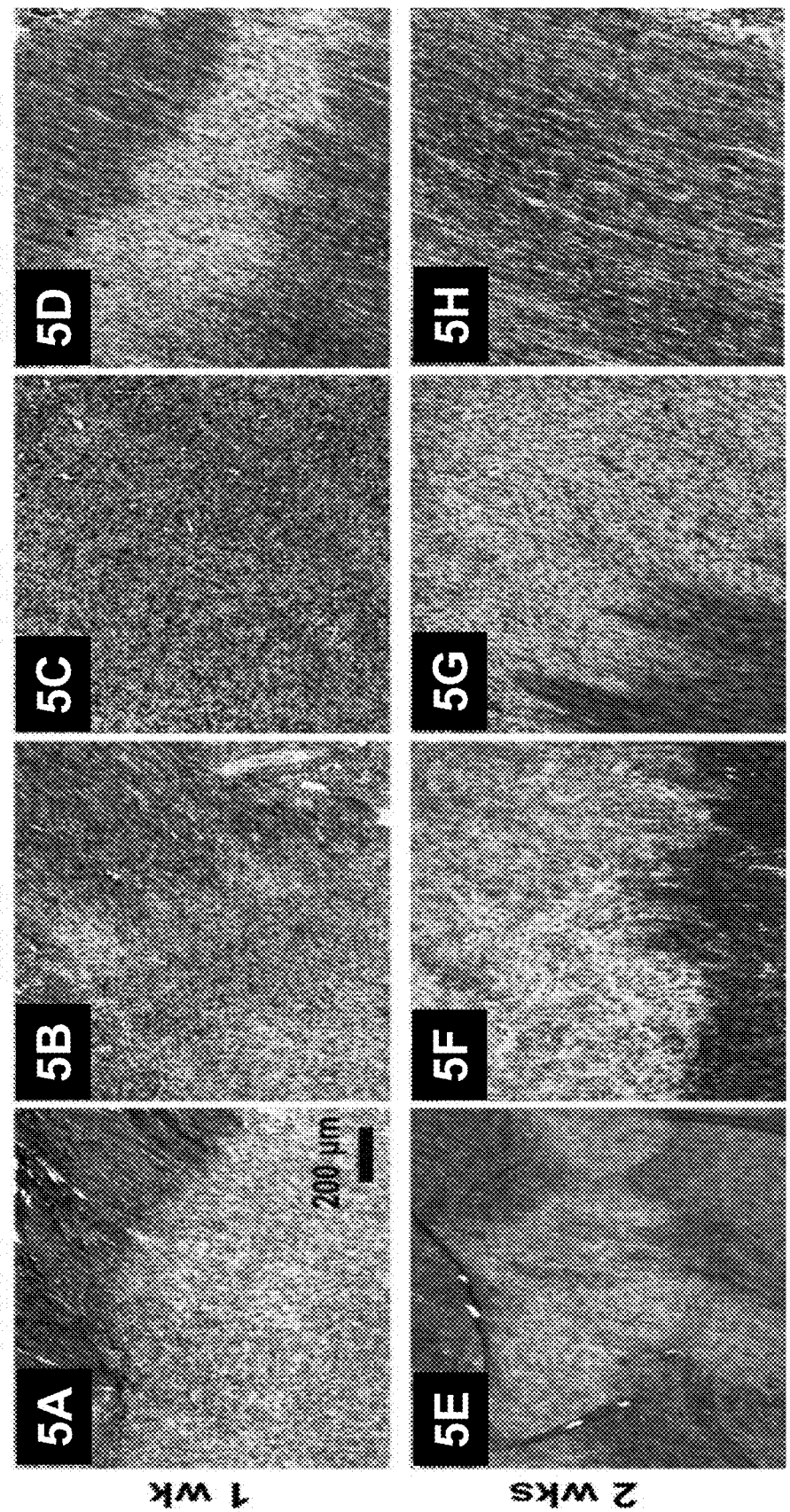
FIG. 5A-5H shows Masson's Trichrome staining of healing zone of tendons. Delivery of Oxo-M (1 mM)+4-PPBP (10 µM) showed more and denser collagen in the healing zone by 2 weeks post-op (FIG. 5H) as compared to disrupted collagen structure with control (FIG. 5E), Oxo-M alone (FIG. 5F), and 4-PPBP alone (FIG. 5G) delivered groups. No major differences were seen between the groups at 1 week post-op (FIG. 5A-D).

Activation of FAK and ERK1/2 signaling by Oxo-M and 4-PPBP was further confirmed by western blot and siRNA knockdown (KD). By 12 hours treatment in PTSCs, 4-PPBP resulted in phosphorylation of FAK, whereas Oxo-M resulted in phosphorylation of FAK and ERK1/2 (FIG. 3A). With combined Oxo-M and 4-PPBP, both P-FAK and P-ERK1/2 were detected (FIG. 3A). In contrast, CD146− tendon cells (excluding PTSCs) showed no P-FAK band when treated by Oxo-M, 4-PPBP, and Oxo-M+4-PPBP (FIG. 3A), suggesting that Oxo-M and 4-PPBP selectively target PTSCs. Consistently, the level of tendon-related gene expressions induced by Oxo-M+4-PPBP in CD146− tendon cells was significantly lower than CD146+ PTSCs. In addition, siRNA KD of FAK and ERK1/2 were performed as described previously (Lee, et al., 2015, supra), which is hereby incorporated herein by reference in its entirety for all purposes. Briefly, FAK and ERK1/2 were knockdown using Silencer® siRNA (100 nM) and Neon® transfection system (Life Technologies) with pre-optimized electroporation conditions (1,400V; 20 mS; 2 pulses). qRT-PCR showed that FAK and ERK1/2 KD significantly attenuated the Oxo-M+4-PPBP-induced Scx expression in PTSCs (FIG. 3B).

Example 2

This Example shows that delivery in vivo of a combination of Oxo-M and 4-PPBP in a rat tendon defect model showed improved tendon healing. The animal model was used to study the in vivo response and development of these tissues from endogenous cells stimulated by Oxo-M and 4-PPBP delivery.

This study was designed to investigate effect of Oxo-M and 4-PPBP on tendon healing. Animals were given Oxo-M alone (1 mM), 4-PPBP alone (10 µM), and a combination of Oxo-M (1 mM)+4-PPBP (10 µM) along with fibrin gel as a vehicle after patellar tendon transection. Fibrin alone served as a vehicle control. Multiple time points (1 and 2 weeks) were selected to follow up the process of healing and remodeling of tendon. Tissue healing, matrix formation and remodeling, and functional restoration were examined using histology, immunohistochemistry, and mechanical testing (tensile) as per prior methods (Lee, et al., *J. Clin. Invest.* 120:3340-3349, 2010; Lee, et al., *Lancet* 376:440-448, 2010; Lee, et al., *Sci. Transl. Med.* 6(266):266ra171, 2014; Lee et al., 2015, supra). Each of these references is incorporated herein in its entirety for all purposes.

The study was designed as follows:

1. Patella tendon was transected. A 10-mm longitudinal incision was made just medial to the knee. Upon exposure of patellar tendon, a full-thickness transverse incision was made on the medial part of tendon from the inferior pole of the patella.

2. Small molecules (Oxo-M and 4-PPBP, alone or in combination) were delivered to the transected tendon via fibrin as a delivery vehicle to see the effect on promoting healing. Fibrin glue, prepared by mixing 1:1 of fibrinogen and thrombin with or without Oxotremorine-M (1 mM), PPBP maleate (10 µM), and Oxo M+4-PPBP was applied on the transection site.

3. Fibrin gel without Oxo-M and 4-PPBP served as a negative control group.

4. At 1 and 2 weeks post-op, the operated animals were euthanized followed by patella tendon collection post mortem for further evaluation.

The data demonstrated a novel function of the combined Oxo-M and 4-PPBP in tendon healing. Oxo-M is a non-selective muscarinic acetylcholine receptor agonist and 4-PPBP is σ1 receptor ligand of which roles in tendon or tendon stem cells have never been reported. Although Oxo-M or 4-PPBP alone showed only minimal effect, the combination of Oxo-M and 4-PPBP showed a notable synergic effect on induced tenogenic differentiation of PTSCs and tendon healing.

FIG. 4A-H shows the healing of the fully transected rat patellar tendons at 1 week post-op after treatment with no small molecules (control; FIG. 4A), Oxo-M alone (FIG. 4B), 4-PPBP alone (FIG. 4C) and the combination of Oxo-M and 4-PPBP (FIG. 4D) and at 2 weeks post-op after treatment with no small molecules (control; FIG. 4E), Oxo-M alone (FIG. 4F), 4-PPBP alone (FIG. 4G) and the combination of Oxo-M and 4-PPBP (FIG. 4H) by H&E staining. At 1 week post-op, delivery of Oxo-M (1 mM)+4-PPBP (10 µM) resulted in reduced gaps and more aligned collagen structure (FIG. 4D), as compared to disorganized scar-like tissue with control (FIG. 4A), Oxo-M (FIG. 4B), and 4-PPBP (FIG. 4C) alone. At 2 weeks, control (FIG. 4E), Oxo-M (FIG. 4F), and 4-PPBP (FIG. 4G) groups ended up with scar-like healing, whereas Oxo-M+4-PPBP (FIG. 4H) showed significantly improved healing with densely aligned fibers.

FIG. 5A-H shows Masson's Trichrome staining of the healing zone of tendons. Delivery of Oxo-M (1 mM)+4-PPBP (10 µM) showed more and denser collagen in the healing zone by 2 weeks (FIG. 5H) as compared to disrupted collagen structure with control (FIG. 5E), Oxo-M (FIG. 5F), and 4-PPBP (FIG. 5G) delivered groups.

FIG. 6A-H shows polarized images of Picrosirius Red stained tendons. Delivery of Oxo-M (1 mM)+4-PPBP (10 µM) showed re-organized collagen fibers by 1 week (FIG. 6D) and 2 weeks (FIG. 6H) as compared to disrupted collagen structure at 1 week and 2 weeks with control (FIG. 6A and FIG. 6E, respectively), Oxo-M (FIG. 6B and FIG. 6F, respectively), and 4-PPBP (FIG. 6C and FIG. 6G, respectively) delivered groups.

FIG. 7A-D shows immunofluorescence for CD146 and COL-I in tendon healing by small molecules at 1 week post-op. The delivery of the combination of Oxo-M and 4-PPBP (FIG. 7D) into tendon healing significantly increased the number of CD146+ PTSCs underdoing differentiation into COL-I+ tenocyte-like cells, as compared to control (FIG. 7A), Oxo-M alone (FIG. 7B) or 4-PPBP alone (FIG. 7C).

Figures 8A, 8B, 8C, 8D:
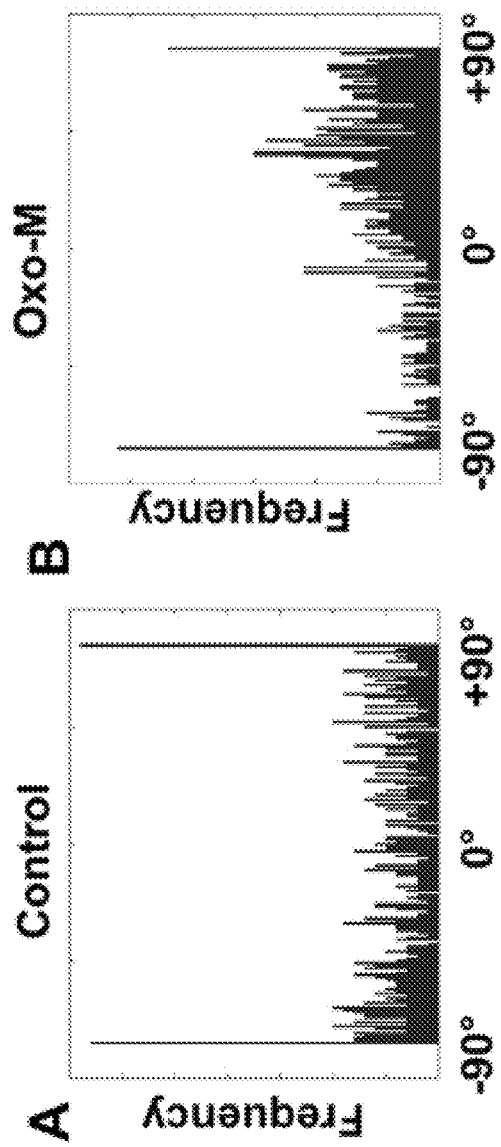
FIG. 8A-8F shows collagen fiber orientation assessed by Picrosirius Red staining with an automated digital image processing for local directionality and angular deviation (AD). Alignment of collagen fibers in the Oxo-M+4-PPBP delivered tendon (FIG. 8D) was similar to that of the native tendon (FIG. 8E), in contrast to disoriented fibers in scar-like tendon with control (FIG. 8A), Oxo-M alone (FIG. 8B), and 4-PPBP alone (FIG. 8C). Quantitatively, the AD of fibers with Oxo-M+4-PPBP was significantly smaller than all the other groups (FIG. 8F). n=6 per samples, *:$p<0.001$ compared to control, Oxo-M, and 4-PPBP, #:$p<0.05$ compared to Oxo-M+4-PPBP.
Figures 8E, 8F:
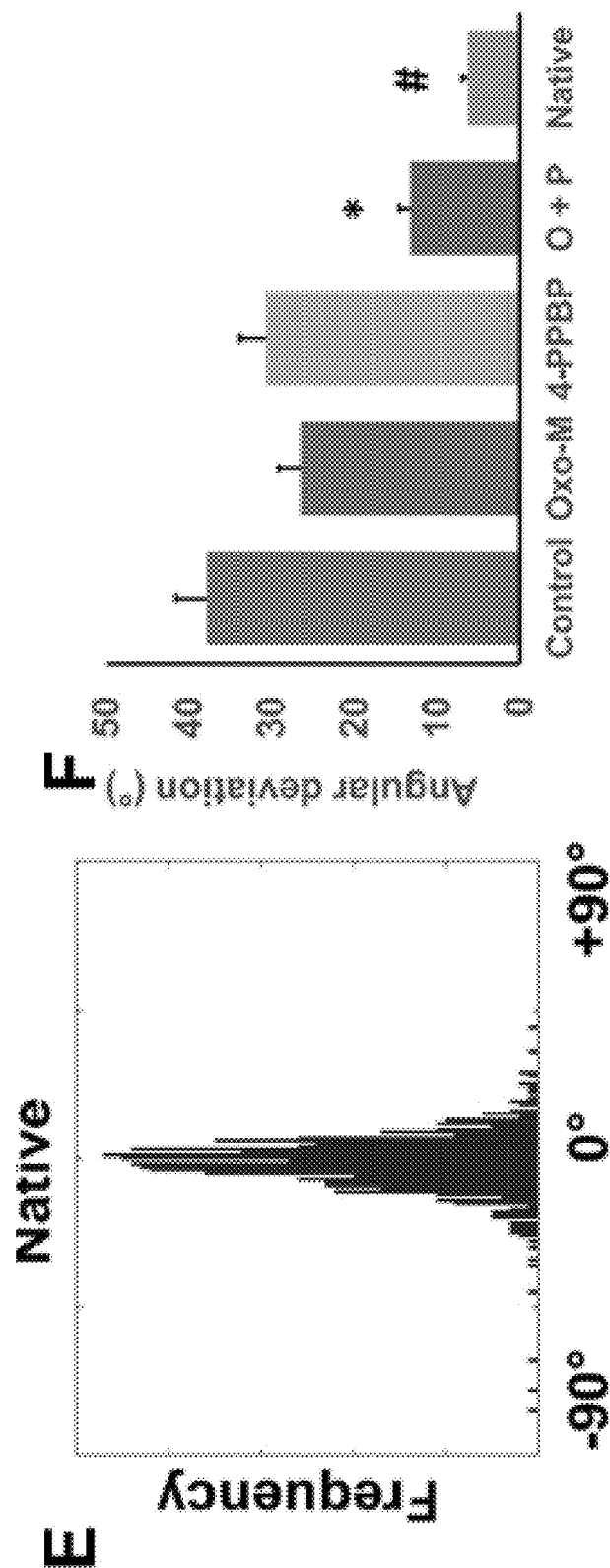

FIG. 8A-F shows collagen fiber orientation assessed by Picrosirius Red staining with an automated digital image processing for local directionality and angular deviation (AD). Alignment of collagen fibers in the Oxo-M+4-PPBP delivered tendon (FIG. 8D) was similar to that of the native tendon (FIG. 8E), in contrast to disoriented fibers in scar-like tendon with control (FIG. 8A), Oxo-M alone (FIG. 8B), and 4-PPBP alone (FIG. 8C). Quantitatively, the AD of fibers with Oxo-M+4-PPBP was significantly smaller than all the other groups (FIG. 8F). n=6 per samples, *:$p<0.001$ compared to control, Oxo-M, and 4-PPBP, #:$p<0.05$ compared to Oxo-M+4-PPBP.

Since Oxo-M and 4-PPBP are FAK and ERK1/2 agonists, respectively, and ERK1/2 is a downstream of FAK signaling, without being limited to any one theory of the invention the synergic effect is likely attributed to the potential cross-talk between intracellular signaling mediators. As compared to growth factors, small molecules have a number of distinct advantages including their convenience to use, no cross-contamination risk, no immunorejection, and fine-tunable biological effects and delivery control. Accordingly, the combination of Oxo-M and 4-PPBP, replacing the CTGF's function in tendon healing via selective signaling pathway, overcomes the limitations related to cell and/or protein delivery for tendon regeneration. The novel combination of Oxo-M and 4-PPBP serves as a focused therapeutics for tendon regeneration in comparison with delivery of stem cells, cytokines, or growth factors.

Example 3

This Example shows that delivery in vivo of a combination of Oxo-M and 4-PPBP in a rat supraspinatus tendon injury model showed improved tendon healing. The animal model was used to study the in vivo response and development of these tissues from endogenous cells stimulated by Oxo-M and 4-PPBP delivery.

This study was designed to investigate effect of a combination of Oxo-M (1 mM)+4-PPBP (10 µM) along with fibrin gel as a vehicle after supraspinatus tendon transection. Fibrin alone served as a vehicle control. Four weeks post-op was selected to follow up the process of healing and remodeling of tendon. Tissue healing, matrix formation and remodeling, and functional restoration were examined using histology as per prior methods (Lee, et al., J. Clin. Invest. 120:3340-3349, 2010; Lee, et al., Lancet 376:440-448, 2010; Lee, et al., Sci. Transl. Med. 6(266):266ra171, 2014; Lee et al., 2015, supra).

The study was designed as follows:

1. Rat supraspinatus tendon was transected at the tendon enthesis, followed by bone abrasion and suture repair through bone tunnels.

2. Small molecules (Oxo-M and 4-PPBP in combination) were delivered to the transected tenson via fibrin as a delivery vehicle to see the effect on promoting healing. Fibrin glue, prepared by mixing 1:1 of fibrinogen and thrombin with or without Oxo M+4-PPBP was applied on the transection site.

3. Fibrin gel without Oxo-M and 4-PPBP served as a negative control group.

4. At 4 weeks post-op, the operated animals were euthanized followed by supraspinatus tendon collection post mortem for further evaluation.

The data demonstrated similar results to that found in the rat patellar study detailed above. The combination of Oxo-M and 4-PPBP showed a notable synergic effect on tendon healing.

Figures 9A, 9B, 9C, 9D, 9E, 9F, 9G, 9H, 9I:
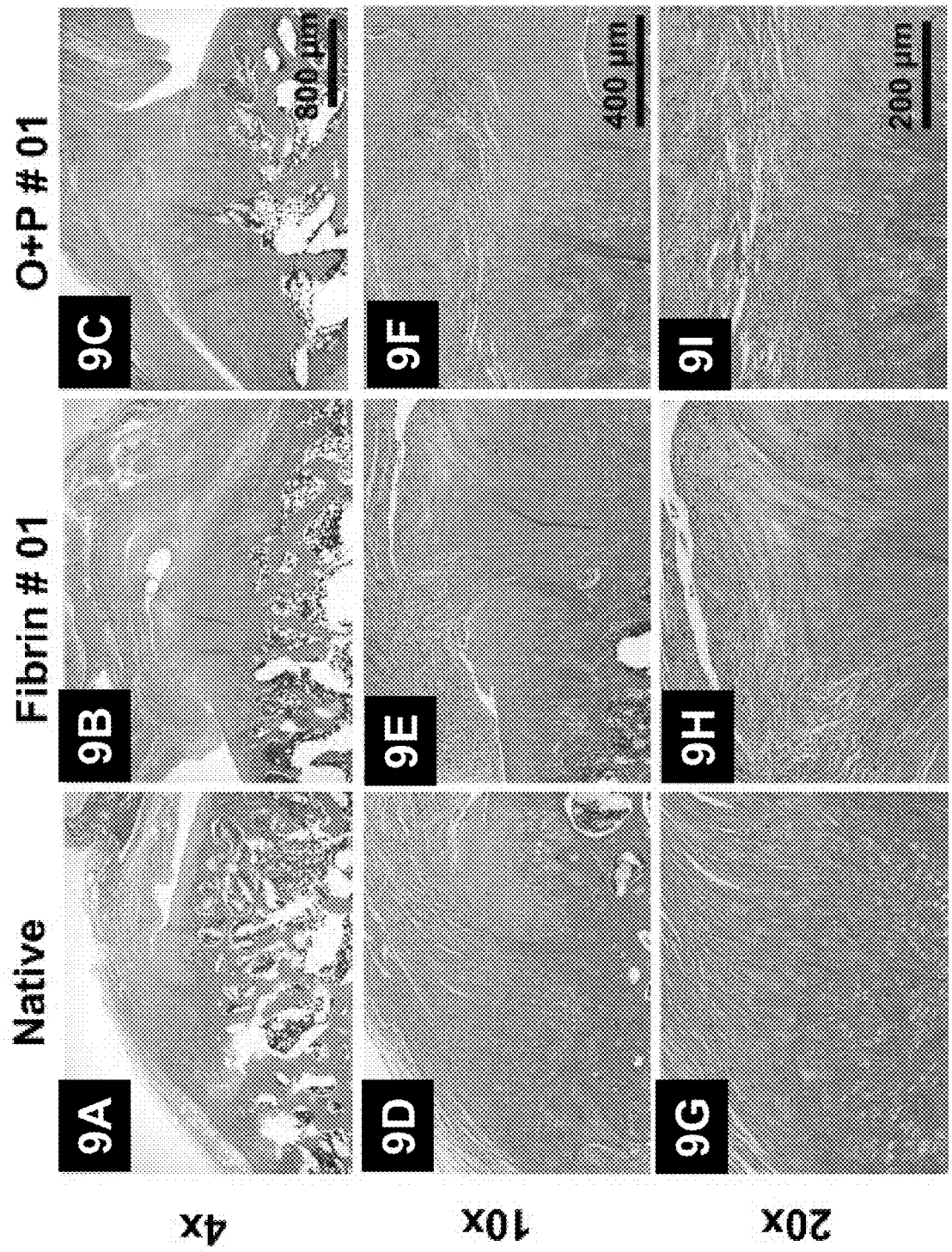
FIG. 9A-9I is a series of H&E stained slides showing healing of transected rat supraspinatus tendons by Oxo-M plus 4-PPBP at 4×, 10× and 20× magnification at 4 weeks post-op. The combination of Oxo-M and 4-PPBP shows repair of transected rat supraspinatus tendons (FIG. 9C, FIG. 9F and FIG. 9I) to more closely resemble native rat supraspinatus tendons (FIG. 9A, FIG. 9D and FIG. 9G) compared to control (FIG. 9B, FIG. 9E and FIG. 9H).

FIG. 9A-I shows native rat supraspinatus tendons at 4× magnification (FIG. 9A), 10× magnification (FIG. 9D) or 20× magnification (FIG. 9G), and the healing of the transected rat supraspinatus tendons at 4 weeks post-op after treatment with fibrin control at 4× magnification (FIG. 9B), 10× magnification (FIG. 9E) or 20× magnification (FIG. 9H) or the combination of Oxo-M and 4-PPBP at 4× magnification (FIG. 9C), 10× magnification (FIG. 9F) or 20× magnification (FIG. 9I). At 4 weeks, Oxo-M+4-PPBP showed significantly improved healing compared to control.

Figures 10A, 10B, 10C, 10D, 10E, 10F, 10G, 10H, 10I:
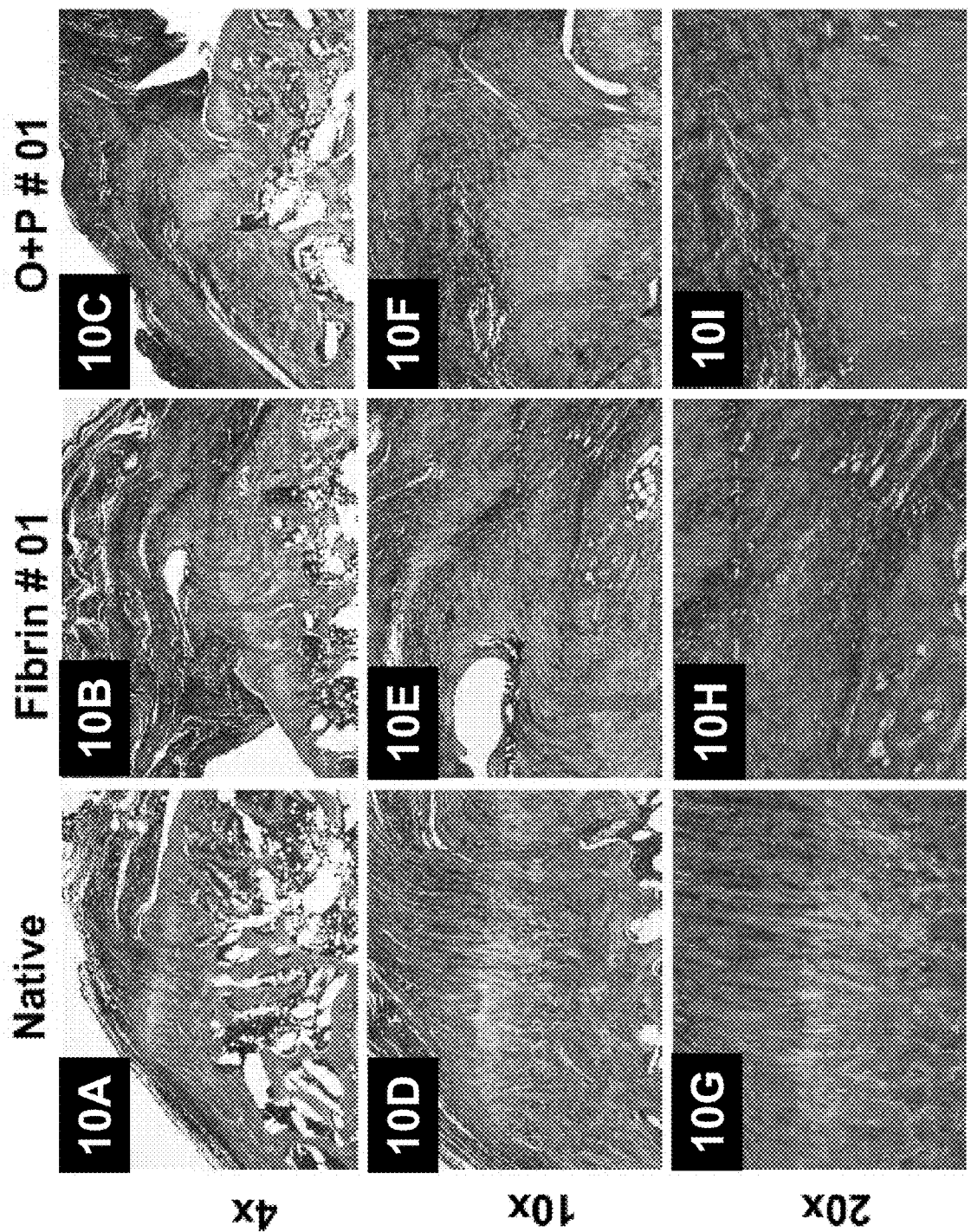
FIG. 10A-10I is a series of Picrosirius Red stained slides showing healing of transected rat supraspinatus tendons by Oxo-M plus 4-PPBP at 4×, 10× and 20× magnification at 4 weeks post-op. The combination of Oxo-M and 4-PPBP shows repair of transected rat supraspinatus tendons (FIG. 10C, FIG. 10F and FIG. 10I) to more closely resemble native rat supraspinatus tendons (FIG. 10A, FIG. 10D and FIG. 10G) compared to control (FIG. 10B, FIG. 10E and FIG. 10H).

FIG. 10A-I shows polarized images of Picrosirius Red stained native rat supraspinatus tendons at 4× magnification (FIG. 10A), 10× magnification (FIG. 10D) or 20× magnification (FIG. 10G), and the healing of the transected rat supraspinatus tendons at 4 weeks post-op after treatment with fibrin control at 4× magnification (FIG. 10B), 10× magnification (FIG. 10E) or 20× magnification (FIG. 10H) or the combination of Oxo-M and 4-PPBP at 4× magnification (FIG. 10C), 10× magnification (FIG. 10F) or 20× magnification (FIG. 10I). Delivery of Oxo-M (1 mM)+4-PPBP (10 μM) showed re-organized collagen fibers as compared to disrupted collagen structure with control.

Figures 11A, 11B, 11C, 11D, 11E, 11F, 11G, 11H, 11I:
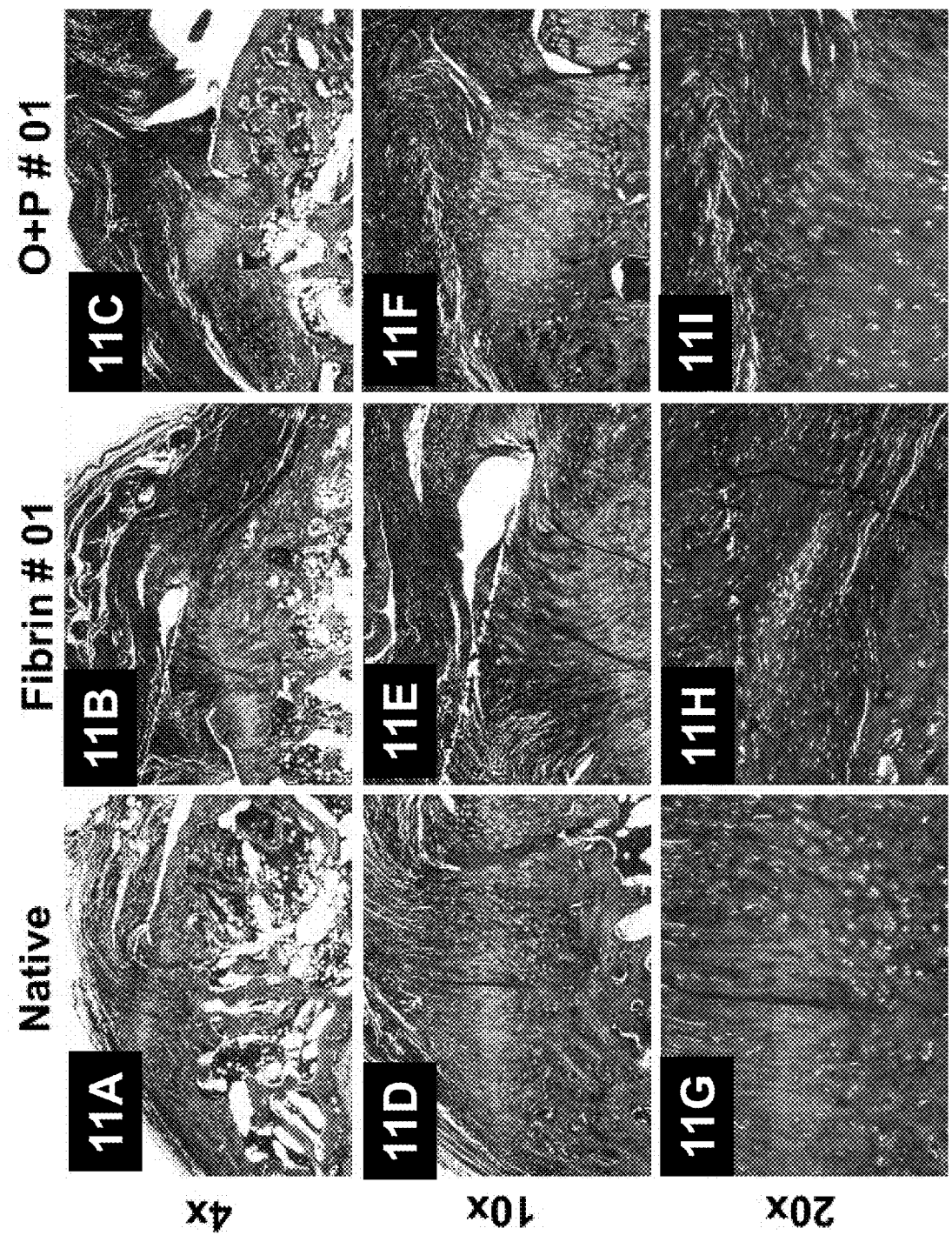
FIG. 11A-11I is a series of Masson's Trichrome stained slides showing healing of transected rat supraspinatus tendons by Oxo-M plus 4-PPBP at 4×, 10× and 20× magnification at 4 weeks post-op. The combination of Oxo-M and 4-PPBP shows repair of transected rat supraspinatus tendons (FIG. 11C, FIG. 11F and FIG. 11I) to more closely resemble native rat supraspinatus tendons (FIG. 11A, FIG. 11D and FIG. 11G) compared to control (FIG. 11B, FIG. 11E and FIG. 11H).

FIG. 11A-I shows Masson's Trichrome staining of the healing zone of native rat supraspinatus tendons at 4× magnification (FIG. 11A), 10× magnification (FIG. 11D) or 20× magnification (FIG. 11G), and the healing of the transected rat supraspinatus tendons at 4 weeks post-op after treatment with fibrin control at 4× magnification (FIG. 11B), 10× magnification (FIG. 11E) or 20× magnification (FIG. 11H) or the combination of Oxo-M and 4-PPBP at 4× magnification (FIG. 11C), 10× magnification (FIG. 11F) or 20× magnification (FIG. 11I). Delivery of Oxo-M (1 mM)+4-PPBP (10 μM) showed more and denser collagen in the healing zone by 4 weeks as compared to disrupted collagen structure with control.

Figures 12A, 12B, 12C, 12D, 12E, 12F, 12G, 12H, 12I:
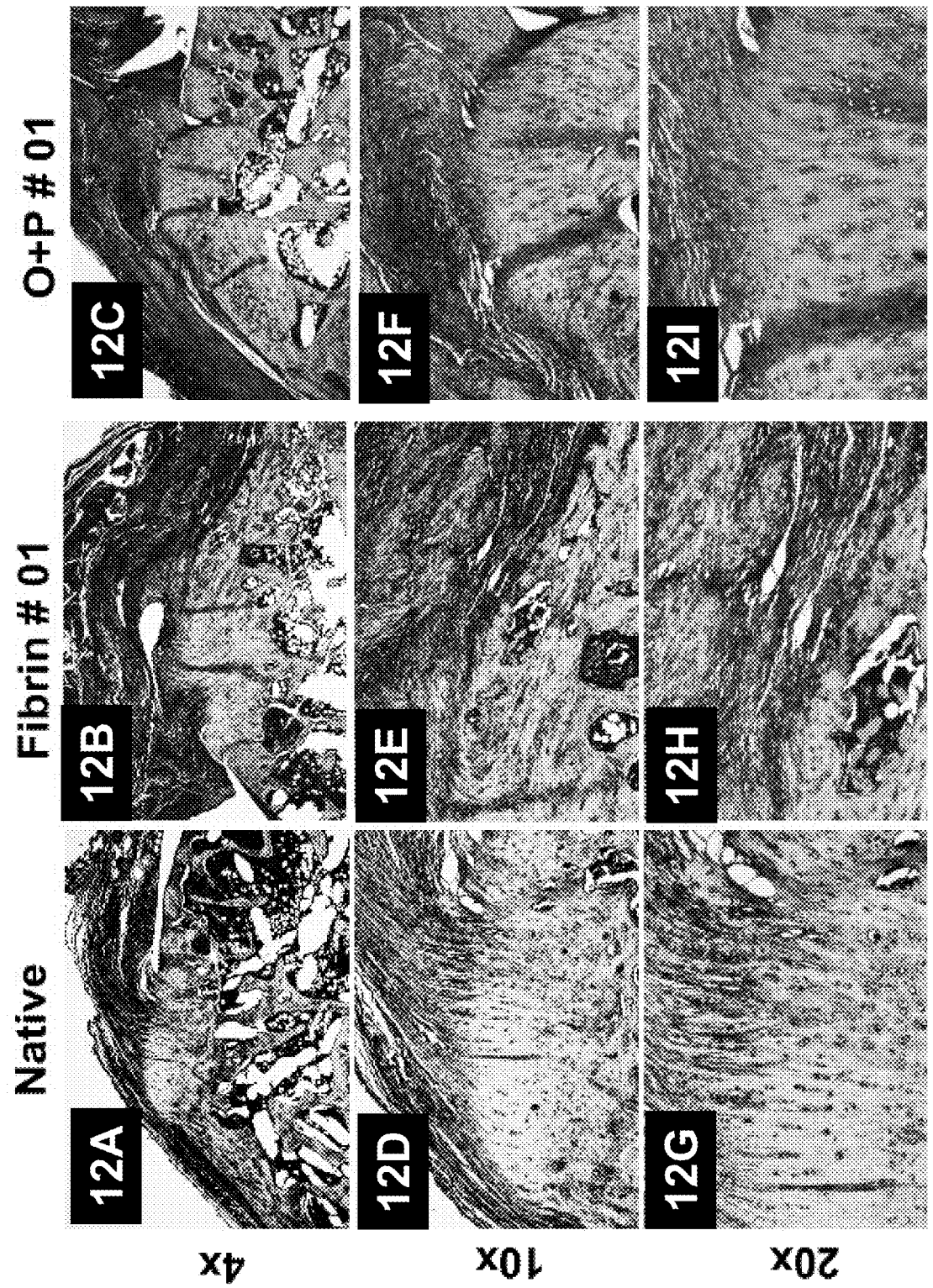
FIG. 12A-12I is a series of Safranin O stained slides showing healing of transected rat supraspinatus tendons by Oxo-M plus 4-PPBP at 4×, 10× and 20× magnification at 4 weeks post-op. The combination of Oxo-M and 4-PPBP shows repair of transected rat supraspinatus tendons (FIG. 12C, FIG. 12F and FIG. 12I) to more closely resemble native rat supraspinatus tendons (FIG. 12A, FIG. 12D and FIG. 12G) compared to control (FIG. 12B, FIG. 12E and FIG. 12H).

FIG. 12A-I shows Safranin O staining of native rat supraspinatus tendons at 4× magnification (FIG. 12A), 10× magnification (FIG. 12D) or 20× magnification (FIG. 12G), and the healing of the transected rat supraspinatus tendons at 4 weeks post-op after treatment with fibrin control at 4× magnification (FIG. 12B), 10× magnification (FIG. 12E) or 20× magnification (FIG. 12H) or the combination of Oxo-M and 4-PPBP at 4× magnification (FIG. 12C), 10× magnification (FIG. 12F) or 20× magnification (FIG. 12I). At 4 weeks, Oxo-M+4-PPBP showed significantly improved healing compared to control.

Example 4

This Example concerns controlled delivery of a combination of Oxo-M and 4-PPBP via poly(lactic-co-glycolic acids) (PLGA) microspheres (μS).

Figure 13:
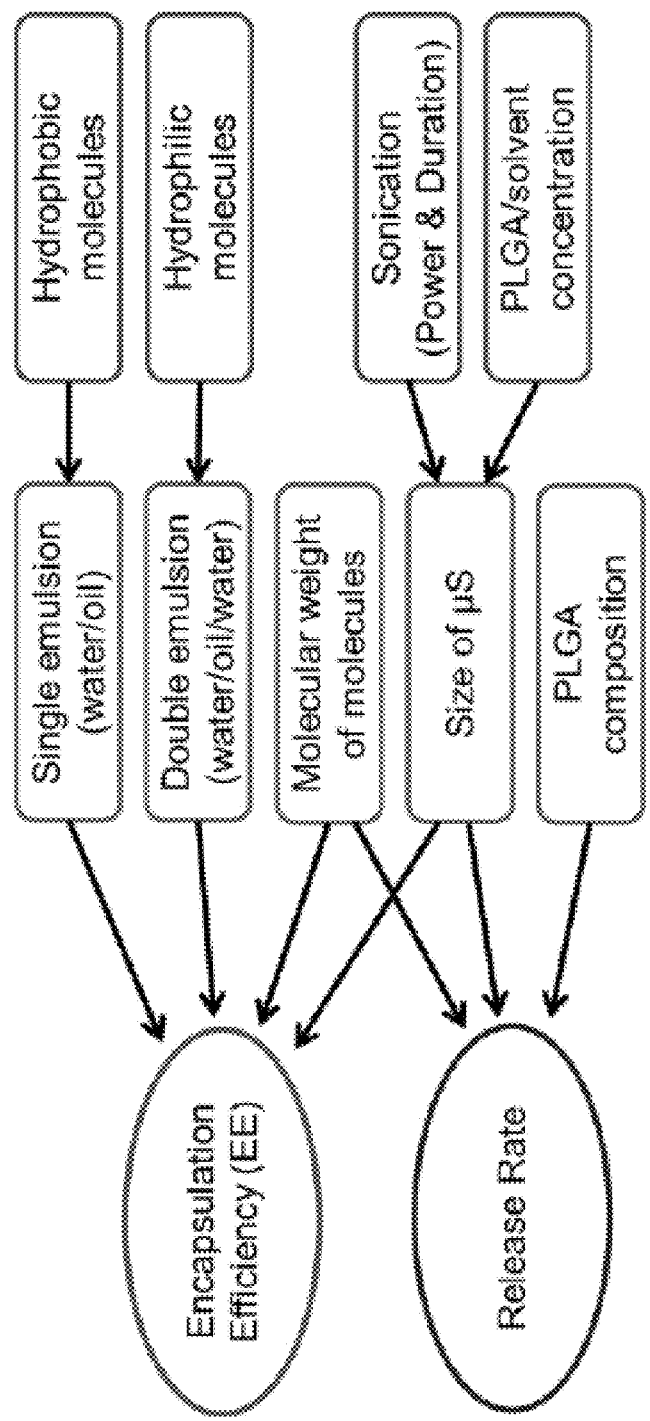
FIG. 13 shows microencapsulation conditions and design parameters as determining factors of EE and release rate (RR) for PLGA microspheres comprising Oxo-M and 4-PPBP.
Figure 14:
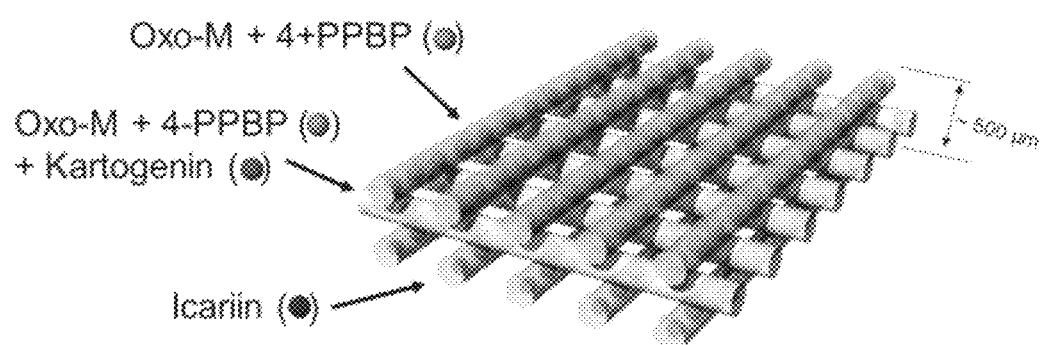
FIG. 14 is an illustration showing a scaffold fabricated with strands having Oxo-M+4-PPBP, Oxo-M+4-PPBP+Kartogenin, and Icariin embedded therein.

PLGA is a widely used biodegradable polymer for preparation of pS loaded with small molecules or growth factors (Lee, et al., 2015, supra). PLGA microspheres encapsulate small molecules or growth factors by a process called "emulsification," and the encapsulated molecules or factors release in a sustained manner as PLGA slowly degrades via hydrolysis. As summarized in FIG. 13, the encapsulation efficiency (EE) and the release rate (RR) of small molecules in PLGA μS are determined by multiple factors, including the emulsification technique, the size of microspheres, the composition of PLGA and the associated degradation rate, and the hydrophilicity/hydrophobicity of the molecules. The key microencapsulation conditions (Table 1) can be tuned to establish a high EE and a prolonged release of Oxo-M and 4-PPBP from PLGA μS for efficient induction of tendon regeneration.

Based on the inventors protocol (Lee, et al., 2014, supra; Lee, et al., 2015, supra; Lee, et al., *Tissue Eng. Part A* 20:1342-1351, 2014b), Oxo-M and 4-PPBP can be encapsulated in PLGA pS with the microencapsulation conditions and parameters listed in Table 1.

TABLE 1

| Microencapsulation Conditions and Parameters | | | |
|---|---|---|---|
| Variables | Determining Factors | Conditions and Parameters | Expected Outcome |
| Size of μS | Ultra-sonication | Frequency: 20 kHz<br>Power: 50, 100, 200, 400 or 600 W<br>Duration: 15 s, 30 s, 1 min, 10 min, 30 min | 50 nm to 200 μm in diameter |
| | PLGA/solvent concentration | 50 mg/mL, 100 mg/mL, 200 mg/mL | |
| Release rate | PLGA composition | Ratio of lactic to glycolic acids: 50:50, 75:25, 85:15 | 80% release in 2-8 wks in sustained manner |
| Encapsulation Efficiency | Size of μS, emulsion technique, MW, PLGA composition | Derived from above parameters | 40-60% of the total applied molecules |

Briefly, PLGA can be dissolved into chloroform at the above-listed concentrations, followed by adding 50 μl diluted Oxo-M (1 mM) or 4-PPBP (10 μM) in distilled water (DW). This solution can then be emulsified (primary emulsion) by ultrasonicating to reduce the size of μS. In order to apply double emulsion for hydrophilic Oxo-M, the primary emulsion (water/oil) can be added to 10 ml 4% (w/v) PVA (poly vinyl alcohol) solution to form the second emulsion (water/oil/water) by ultrasonication, followed by 1 min vortexing. The primary-emulsion (4-PPBP) or double-emulsion solution (Oxo-M) can then be added to 250 ml of 0.3% PVA solution followed by continuous stirring for 2 h to evaporate the solvent. Finally, the μS can be filtered, washed with DI water for 3 times, resuspended in DI water and then lyophilized. The size of PLGA μS can be analyzed using SEM (ZEISS SUPRA 55VP) as previously described (Lee, et al., 2014, supra; Lee, et al., 2015, supra; Lee, et al., 2014b, supra). The EE can be measured by dissolving 10 mg of PLGA μS in chloroform, followed by measuring concentration of Oxo-M or 4-PPBP by High Performance Liquid Chromatography (HPLC). For analysis of the release rate, 10 mg of PLGA μS can be incubated in PBS with a gentle agitation. At the selected time points, the incubation buffer

Example 5

This Example concerns in vivo application of the controlled delivery of a combination of Oxo-M and 4-PPBP via poly(lactic-co-glycolic acids) (PLGA) microspheres (μS) for tendon regeneration.

Once establishing a set of PLGA microencapsulation conditions and resulted EE and release rates, PLGA μS-loaded with Oxo-M and 4-PPBP with slow, intermediate, and fast release rates can be applied to the in vivo tendon healing model detailed above. Various doses of PLGA pS (10, 50, 100 mg/mL) with different release rates can be delivered via a fibrin gel into fully transected rat patella tendon (PT) as detailed above. Briefly, a 10-mm longitudinal incision can be made just medial to the knee. Upon exposure of the patellar tendon, a full-thickness transverse incision can be made using a No. 11 blade scalpel. Fibrin gel, prepared by mixing 1:1 of fibrinogen (50 mg/mL) and thrombin (50 U/mL) with or without selected small molecules at the optimized doses can be applied on the transection site using Fibrijet® dual injector. A 2-0 Ethibond suture (Ethicon Inc, Somerville, N.J., USA) can then be passed through the tibia and quadriceps in a cerclage technique. The surgical site can then be closed using 4.0 absorbable (continuous stitch) for the subcutaneous layer and 4.0 PDS and monocryl (interrupted stitches) for the skin closure. At multiple time points (1-4 wks), animals can be euthanized and the quality of tendon healing in association with endogenous PTSCs can be analyzed as described in Example 2 above.

Statistical comparisons between the control and the small molecules (±μS) group can be made for all the data available for quantification, including the digitally analyzed collagen orientation under polarized images (angular deviation: AD), the ratio and number of markers-expressing PTSCs, and mechanical properties. At least 10 biological replicates, based on the Power analysis below, can be included for all the statistical analyses of the outcome from randomly selected tissue sections as well as tissue samples for mechanical tests. CTGF delivery can be used as a positive control for the in vivo studies.

As detailed above, a series of mechanical tests can be performed for functional characterization of the regenerated tendons, using Electroforce® Biodynamic® test system (Bose Corp., Eden Prairie, Minn.) following established protocols for testing tendon's mechanical properties as detailed above (Lee, et al., 2015, supra). The muscle-tendon-bone complexes can be harvested and prepared as described (Lee, et al., 2015, supra), clamped with tensile jigs, and preconditioned for 10 cycles at 0.1 Hz between 5N and 10N as maintaining 100% humidity. For tensile properties, a constant displacement rate at 0.25 mm/sec can be applied until failure. Elongation can be measured by the embedded displacement sensor and a Digital Video Extensometer (DVE), and force curve can be recorded via the embedded load-cell. From force-displacement curve, stiffness, maximum force, failure displacement can be calculated. For stress-relaxation test, a load of 30N can be applied and the final displacement can be held constant while the declining load is measured at 4 Hz either for 15 minutes or until the load changed less than 0.1 percent over 1 minute, and peak and relaxation moduli and coefficient of relaxation can be calculated.

Example 6

This Example concerns in vivo application of the controlled delivery of a combination of Oxo-M and 4-PPBP via poly(lactic-co-glycolic acids) (PLGA) microspheres (μS) in tendinopathy models.

Upon confirmation of the improved healing of transected rat PT, controlled co-delivery of Oxo-M and 4-PPBP can be applied for pathological tendon models that more closely replicate the chronic effects of tendon injury/disease. Pathological conditions have been created in tendons at multiple anatomical locations (e.g., PT, rotator cuff, and Achilles) by mechanical overuse (Lake, et al., *Disabil. Rehabil.* 30:1530-1541, 2008; Lui, et al., *Scand. J. Med. Sci. Sports* 21:3-17, 2011) or genetic modifications. The overuse-induced tendinopathy in rat PT can be adopted first, featured by hypercellularity, disorganized collagen fibers, increased cartilaginous matrix, decreased mechanical properties, elevated inflammation and MMP activities, and impaired healing upon acute injury. The tendinopathy can be induced in 30 week-old SD rats by a repetitive exercise protocol that consists of treadmill running at 17 m/min on a 10° decline for 1 hour/day, 5 days/week using a rodent treadmill (Exer-3/6 Open Treadmill). After 4-6 weeks of treadmill running, pathological changes in the PT can be evaluated by histology/immunohistochemistry and biochemical assays. To determine effect of Oxo-M and 4-PPBP on prevention of tendon pathology, peritendinous injection of Oxo-M+4-PPBP μS can be made into the tendons with a 27 gauge needle and a 100 μL syringe prior to starting the treadmill exercise. Control animals can receive saline injections with empty μS in the same volume. Then a series of measurements can be made to determine effects of the Oxo-M+4-PPBP μS injections on the progress of tendinopathy, the number and bioactivities of PTSCs, the expression patterns of pro- and anti-inflammatory cytokines (IL-1β, IL-6, IL-10), MMPs (−1, −3, −8, −9) and TIMPs (−1, −2, −3, −4), and mechanical properties of tendons as described above. In parallel, Oxo-M+4-PPBP μS can also be applied for healing of pathological tendons that has further-impaired healing capacity. Briefly, tendons that undergo mechanical overuse for 6 weeks can be fully transected, followed by repair with cerclage suture. Then Oxo-M+4-PPBP μS can be delivered to the repaired tendons via fibrin gel as described above. By 1-6 weeks post-op, the quality of tendon healing in association with endogenous PTSCs can be analyzed as described in Example 2 above.

All quantitative data in the in vitro and in vivo experiments can be subjected to statistical analysis. For normal data distribution, the Analysis of Variance (ANOVA) with Bonferroni tests can be used. For skewed data distribution, nonparametric tests such as Kruskal-Wallis analysis of variance can be used with $\alpha=0.05$. Power analysis: Sample numbers for all the in vitro and in vivo experiments can be determined by Power analysis with a significance level of 0.05 and effect size of 1.50. Estimated outcome for power analysis can be adopted as described for soft tissue regeneration (Lee, et al., 2014, supra). Sample numbers of 8 and 10 per group can be estimated from power analysis for in vitro and in vivo experiments, respectively.

What is claimed is:

1. A composition comprising oxotremorine M (Oxo-M) and PPBP maleate (4-PPBP).

2. The composition of claim 1, wherein the concentration of Oxo-M ranges from 10 µM to 100 mM.

3. The composition of claim 2, wherein the concentration of Oxo-M ranges from 100 µM to 10 mM.

4. The composition of claim 3, wherein the concentration of Oxo-M is 1 mM.

5. The composition of claim 1, wherein the concentration of 4-PPBP ranges from 100 nM and about 1 mM.

6. The composition of claim 5, wherein the concentration of 4-PPBP ranges from 1 µM and about 100 µM.

7. The composition of claim 6, wherein the concentration of 4-PPBP is 10 µM.

8. The composition of claim 1, wherein the concentration of Oxo-M is 1 mM and the concentration of 4-PPBP is 10 µM.

9. A pharmaceutical composition comprising:
oxotremorine M (Oxo-M);
PPBP maleate (4-PPBP); and
a pharmaceutically acceptable excipient.

10. The pharmaceutical composition of claim 9, wherein the concentration of Oxo-M is 1 mM and the concentration of 4-PPBP is 10 µM.

11. The composition of claim 1 further comprising a matrix material, a surgical adhesive, or a fibrin glue.

12. The composition of claim 1 further comprising an antibiotic, an anti-inflammatory, a cytokine, a growth factor, or a stem cell.

13. The composition of claim 1, wherein said Oxo-M and said 4-PPBP are encapsulated in a microsphere.

14. A method of treating a connective tissue defect in a subject, the method comprising:
administering a therapeutically effective amount of the composition of claim 1 to said subject.

15. The method of claim 14, wherein said connective tissue defect comprises a tendon injury or a ligament injury.

16. The method of claim 15, wherein said connective tissue defect comprises a tendon injury.

17. The method of claim 16, wherein said tendon injury is a patellar tendon injury, an Achilles tendon injury, a rotator cuff injury, or lateral epicondylitis.

18. The method of claim 14, wherein said subject is a human subject.

19. A kit comprising a first container containing Oxo-M and a second container containing 4-PPBP.

20. The kit of claim 19, further comprising a third container containing a matrix material, a surgical adhesive, or a fibrin glue.

21. The kit of claim 19 further comprising an antibiotic, an anti-inflammatory, a cytokine, a growth factor, or a stem cell.

* * * * *